US012686698B2

United States Patent

Lunstad et al.

(12) United States Patent
(10) Patent No.: US 12,686,698 B2
(45) Date of Patent: Jul. 21, 2026

(54) FAST DEPROTECTING N-EXOCYCLIC AMINO CYCLIC HYDROCARBON PROTECTED GROUPS FOR NUCLEOSIDE PHOSPHORAMIDITES

(71) Applicant: AGILENT TECHNOLOGIES, INC., Santa Clara, CA (US)

(72) Inventors: Benjamin D. Lunstad, Boulder, CA (US); Douglas J. Dellinger, Boulder, CA (US); Robert Kaiser, Santa Clara, CA (US)

(73) Assignee: AGILENT TECHNOLOGIES, INC., Santa Clara, CA (US)

(*) Notice: Subject to any disclaimer, the term of this patent is extended or adjusted under 35 U.S.C. 154(b) by 1010 days.

(21) Appl. No.: 17/681,731

(22) Filed: Feb. 26, 2022

(65) Prior Publication Data

US 2022/0275019 A1 Sep. 1, 2022

Related U.S. Application Data

(60) Provisional application No. 63/154,691, filed on Feb. 27, 2021.

(51) Int. Cl.

*C07H 23/00* (2006.01)
*C07H 19/16* (2006.01)
*C07H 19/207* (2006.01)
*C07H 21/02* (2006.01)

(52) U.S. Cl.

CPC ............ *C07H 23/00* (2013.01); *C07H 19/16* (2013.01); *C07H 19/207* (2013.01); *C07H 21/02* (2013.01)

(58) Field of Classification Search

None

See application file for complete search history.

(56) References Cited

U.S. PATENT DOCUMENTS 5,179,200 A 1/1993 Molko et al.

FOREIGN PATENT DOCUMENTS

| | | | |
|---|---|---|---|
| CN | 1418111 A | | 5/2003 |
| FR | 2 621 591 A1 | | 4/1989 |
| WO | WO 2001/054731 | | 8/2001 |
| WO | WO 2010/034024 A2 | | 3/2010 |

OTHER PUBLICATIONS

Caruthers, M. H., et al. "[15] Chemical synthesis of deoxyoligonucleotides by the phosphoramidite method." Methods in enzymology. vol. 154. Academic Press, 1987. 287-313.*

Carter et al. J. Org. Chem. (2000), vol. 65, pp. 8375-8378.*

Dellinger et al., "Streamlined Process for the Chemical Synthesis of RNA Using 2'-O-Thionocarbamate-Protected Nucleoside Phosphoramidites in the Solid Phase," *J. Am. Chem. Soc.*, 133:11540-11556, (2011).

Hasan et al., "Photolabile Protecting Groups for Nucleosides: Synthesis and Photodeprotection Rates," *Tetrahedron*, vol. 53, No. 12, pp. 4247-4264, (1997).

International Search Report and Written Opinion issued in corresponding PCT Application No. PCT/US2022/018044, mailed on Jun. 9, 2022.

Jagtap et al., "2-(N-acyl) and 2-N-acyl-N(6)-substituted analogues of adenosine and their affinity at the human adenosine receptors," Bioorg Med Chem Lett, 14(6):1495-8, (2004).

Sachdev and Starkovsky, "Enzymatic Removal of Acyl Protreting Groups, The Use of Dihydro-Cinnamoyl Group in Oligonucleotide Synthesis and its Cleavage By a-Chymotrypsin," *Tetrahedron Letters*, No. 9, pp. 733-736, (1969).

Varaprasad, "A New Protecting Group for the Exocyclic Amino Group of Nucleosides," *Tetrahedron Letter* 46: 2163-2165, (2005).

Written Opinion of the International Preliminary Examining Authority issued in corresponding PCT Application No. PCT/US2022/018044, mailed on Jan. 12, 2023.

Office Action issued in Chinese Patent Application No. 202280016811.3, dated Mar. 17, 2026 (with machine translation).

Office Action issued in Japanese Patent Application No. 2023-550677, dated Apr. 7, 2026 (with machine translation).

* cited by examiner

*Primary Examiner* — Patrick T Lewis

(57) ABSTRACT

Compounds useful for forming nucleic acids having the structure of Formula I:

Formula I

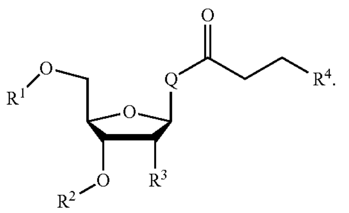

Each of $R^1$ or $R^2$ is independently selected from hydrogen, a protecting group, or a phosphoramidite group. $R^3$ is selected from H, F, O—$C_{1-6}$ alkyl, O-MOE and a removable hydroxyl-protecting group. Q is a heterocyclic base. $R^4$ is a cyclic hydrocarbon. Also disclosed are processes for forming the nucleic acids from the compounds and the nucleic acid products produced.

18 Claims, 6 Drawing Sheets

FIGURE 2: Deprotection of 100mer RNA synthesized with rG(hcin)
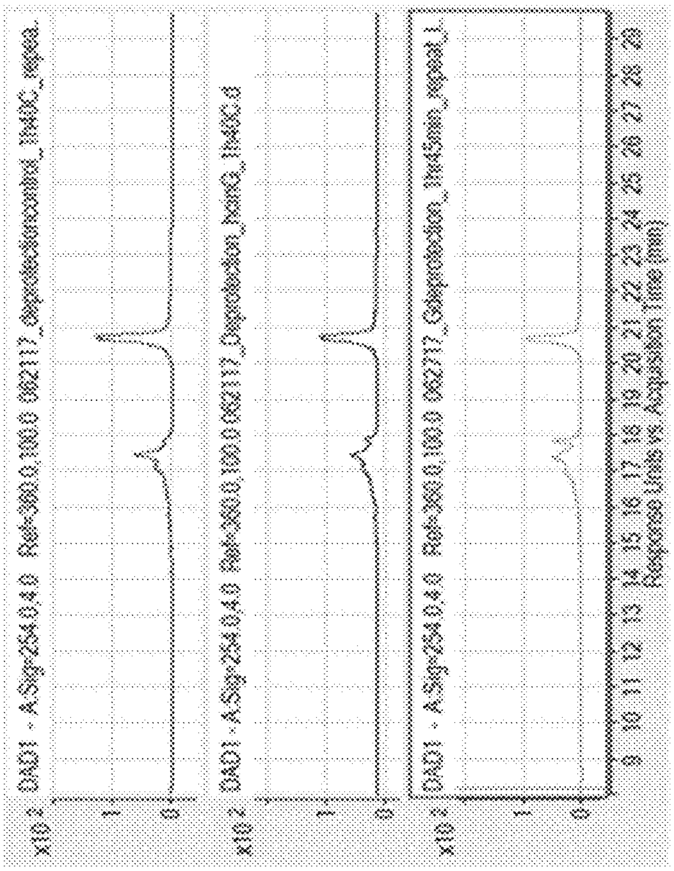
Deprotection of 100-mer RNA at 40°C for 1h (control-iBuG)
Deprotection of 100-mer RNA at 40°C for1h (hcinG)
Deprotection of 100-mer RNA at RT for1h45 min (hcinG)

FIGURE 3: Deprotection Kinetics – 20mer RNA
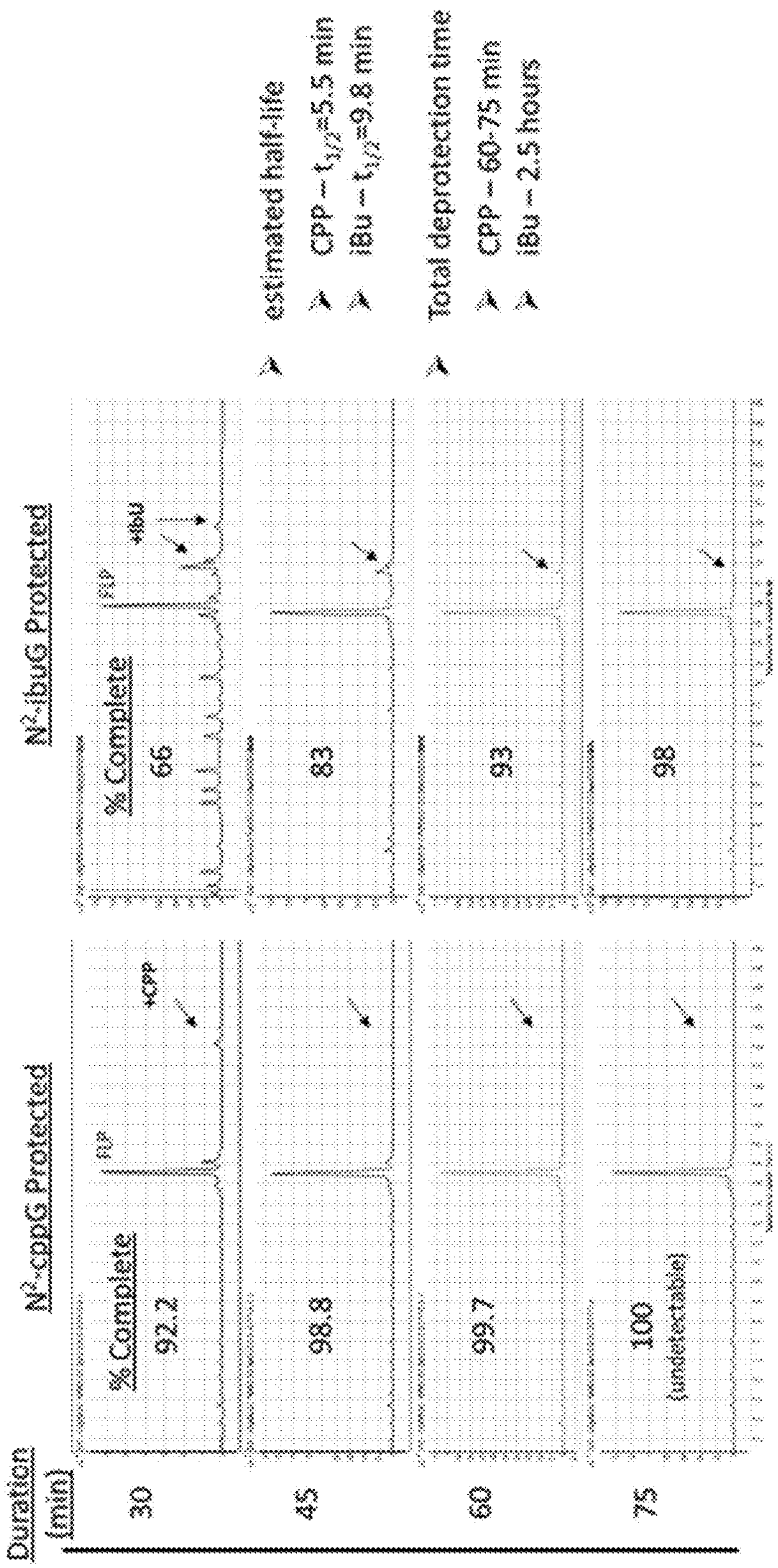

FIGURE 4: Deprotection Kinetics – 100mer RNA
- No change in purity profile between 75 – 90 min, indicating cpp deprotection has reached completion.
- No change in purity profile between 120 – 150 min
- Note longer time course
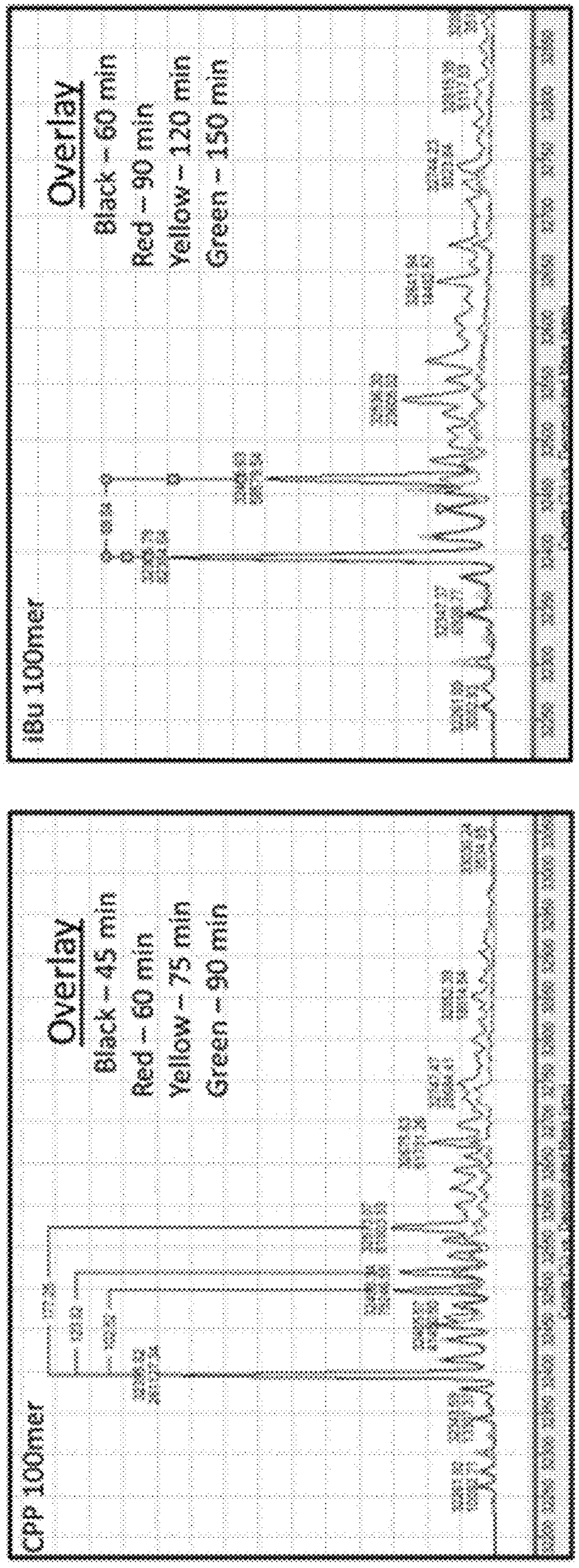

FIGURE 5: Effect of RNA deprotection time on RNA %FLP
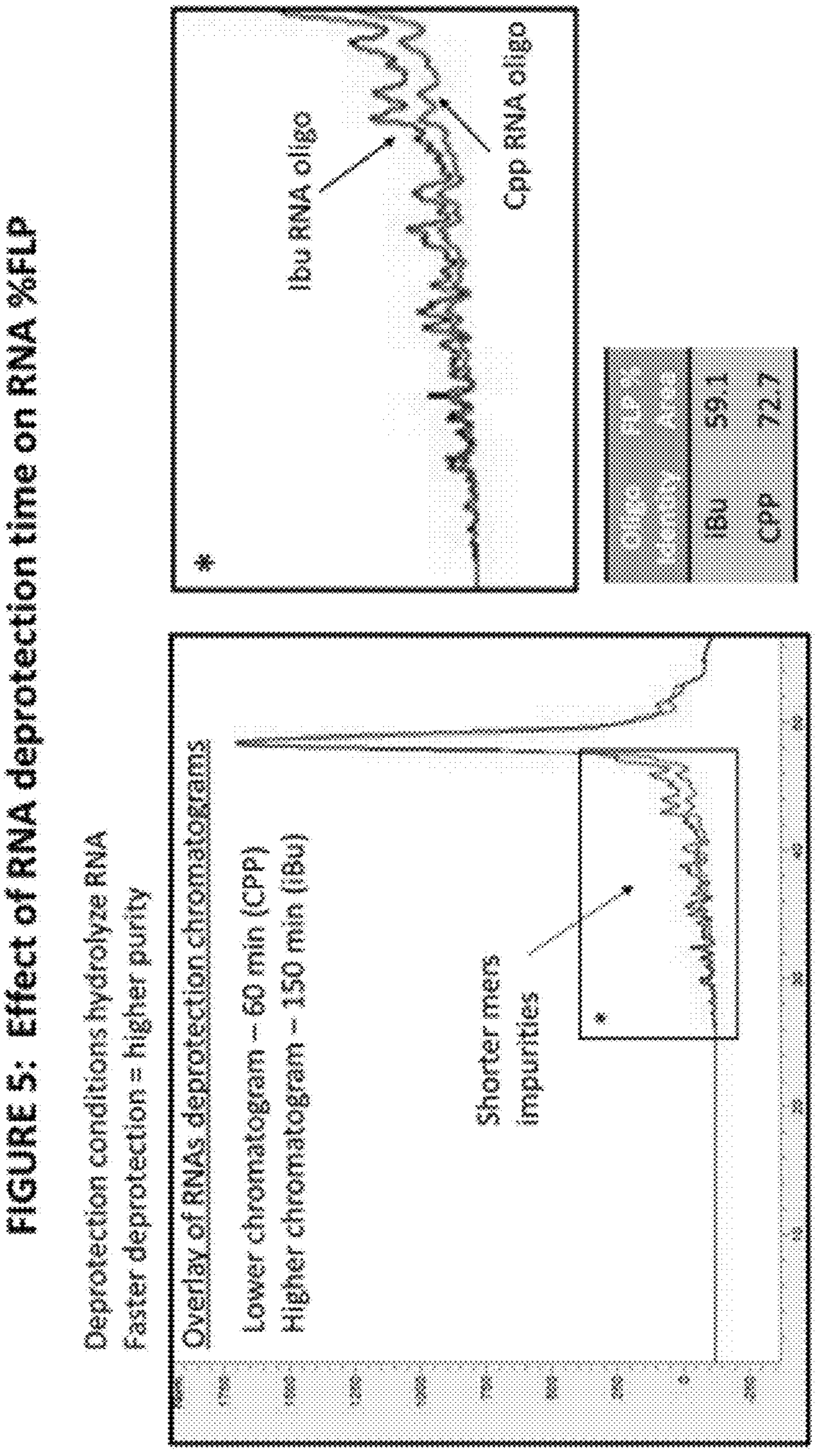

FIGURE 6: Depyrimidination Impurities Profiles Comparison
Mass Spectrometry scans overlay
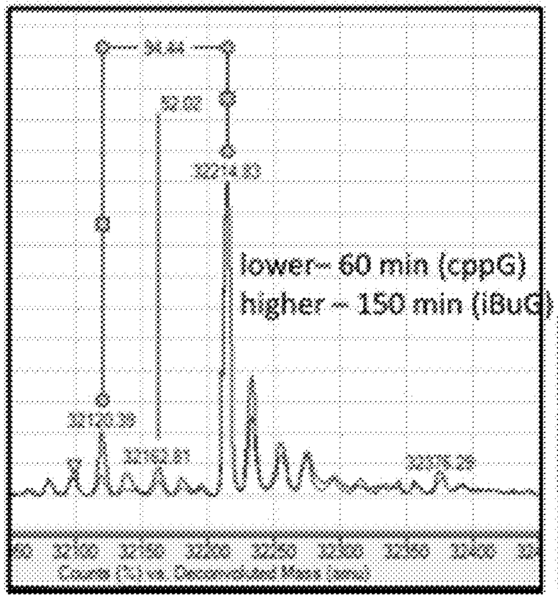
The depyrimidination impurities peaks area are decreased by ~50% in the cppG-containing oligos compared to the ibuG containing oligos.
| Impurity Identity | Impurity % Area (cpp) | Impurity % Area (ibu) |
|---|---|---|
| Depyrimidination (-94 amu) | 7.9 | 18.4 |
| Depyrimidination (-52 amu) | 6.4 | 11.6 |

FAST DEPROTECTING N-EXOCYCLIC AMINO CYCLIC HYDROCARBON PROTECTED GROUPS FOR NUCLEOSIDE PHOSPHORAMIDITES

CROSS-REFERENCE TO RELATED APPLICATIONS

This application claims the benefit of U.S. Provisional Application No. 63/154,691, filed Feb. 27, 2021. The contents of the aforementioned application are hereby incorporated by reference in their entirety.

TECHNICAL FIELD

The present disclosure provides nucleoside monomers having an exocyclic amino heterocycle protecting group. The exocyclic amino heterocycle protecting groups of particular interest include a cycloalkanepropanoyl group, or a hydrocinnamoyl group. Also disclosed are nucleic acids that include the exocyclic amino heterocycle protecting group and methods of synthesizing nucleic acids using the exocyclic amino heterocycle protecting group.

INTRODUCTION

In the discussion of the background that follows, reference is made to certain structures and/or methods. However, the following references should not be construed as an admission that these structures and/or methods constitute prior art. Applicant expressly reserves the right to demonstrate that such structures and/or methods do not qualify as prior art.

Chemical synthesis of RNA is a much more difficult task than chemical synthesis of DNA, because the 2'-hydroxyl group in the ribose has to be protected during chemical synthesis. The close proximity of a protected 2'-hydroxyl to the internucleotide phosphate presents problems, both in terms of formation of the internucleotide linkage and in the removal of the 2'-protecting group once the oligoribonucleotide is synthesized. In addition, the internucleotide bond in RNA is far less stable than that in DNA.

Oligo deprotection includes cleavage of the chemically synthesized oligo from solid support and removal of the protecting groups from the phosphate backbone and nucleobases. The goal of this process is to liberate a completely deprotected oligo without damaging it in the process. Since all deprotection protocols require basic conditions that can damage DNA and RNA, it is beneficial to use protecting groups that allow the use of milder bases and shorter deprotection times while fully protecting the oligo during synthesis. The primary impurities created during deprotection are rU depyrimidination and hydrolysis of the phosphodiester bond.

The typical approach to RNA synthesis utilized ribonucleoside monomers in which the 5'-hydroxyl group was protected by the acid-labile 4,4'-dimethoxytrityl (DMT) protecting group, which can be removed under acidic conditions after coupling of the monomer to the growing oligoribonucleotide. Various acid-stable protecting groups have been placed on the 2'-hydroxyl to prevent isomerization and cleavage of the internucleotide bond during the acid deprotection step. The most popular of these acid-stable protecting groups seems to be the tert-butyl-dimethylsilyl group, known as TBDMS (Ogilvie et al., 1979). The use of TBDMS as 2'-protecting group dominated the previously small market for RNA chemical synthesis for a very long time (Usman et al., 1987; Ogilvie et al., 1988).

Recently, 2'-O-thiomorpholine-4-carbothioate (TC) group was introduced as an alternative RNA 2'-hydroxyl protection chemistry. It uses a simple, one-step deprotection method that removes both the 2'-TC and nucleobases protection at the same time. An exocyclic amine nucleobase protection used currently is isobutyryl (iBu). Post-synthesis, exposure of the oligonucleotide to anhydrous ethylenediamine (EDA) for 5 hours at room temperature, or 1 hour at 40° C., is used for this one-step post-synthesis global deprotection (ie, nucleobases, phosphorous and 2'-hydroxyl deprotection, all at once), but results in detectable amounts of rU depyrimidination depending on the length of RNA being synthesized, due to the time required to remove the isobutyryl groups. Thus, the limitation factor in this deprotection scheme is the complete removal of all the nucleobase exocyclic amine isobutyryl groups. All other protecting groups are more labile than TC, which defines the minimum time required for deprotection. Accordingly, there is a desire to find a more labile protecting group than isobutyryl.

Although there have been some attempts to find exocyclic amine protecting groups more labile than isobutyryl and TC, there has been difficulty in the synthesis of the corresponding ribonucleotides monomers (particularly rG) as 2'-TC amidite due to solubility issues and related 2' to 3' TC isomerization. Accordingly, there remains a need for compounds with a more labile protecting group of the nucleobase exocyclic amine, such as guanine and cytosine that is suitably hydrophobic.

SUMMARY

The present disclosure provides nucleoside monomers having an exocyclic amino heterocycle protecting group. The exocyclic amino heterocycle protecting groups of particular interest include a cycloalkanepropanoyl group, or a hydrocinnamoyl group. Also disclosed are nucleic acids that include the exocyclic amino heterocycle protecting group and methods of synthesizing nucleic acids using the exocyclic amino heterocycle protecting group.

An aspect includes a compound having the structure of Formula I:

Formula I

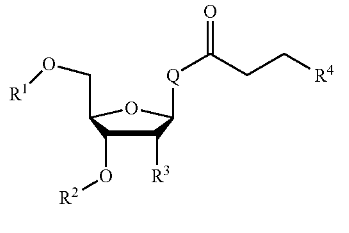

wherein each of $R^1$ or $R^2$ is independently selected from the group consisting of hydrogen, a protecting group, and a phosphoramidite group;

wherein $R^3$ is selected from the group consisting of H, F, O—$C_{1-6}$ alkyl, O-MOE, and a hydroxyl-removable protecting group;

wherein Q is a heterocyclic base; and wherein $R^4$ is a cyclic hydrocarbon.

In embodiments of the compound represented by Formula I, $R^3$ is H, F, O—$C_{1-6}$ alkyl, O-MOE, and a hydroxy-removable protecting group. An example of O—$C_{1-6}$ alkyl group is O—$CH_3$. An example of the removable protecting group is a O-thiocarbon protecting group. Examples of the thiocarbon protecting group include, but are not limited to, thiocarbonates, thionocarbonates, and thionocarbamates. Embodiments of these compounds include compounds of the following structures:

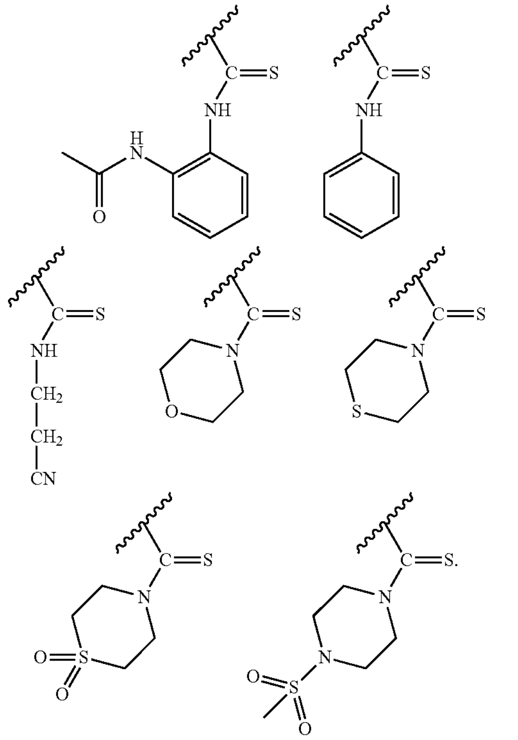

wherein the wiggly line indicates the point of attachment of the thionocarbamate group to the oxygen on the 2' carbon of the nucleotide. In certain embodiments, the O-thiocarbon protecting group is TC:

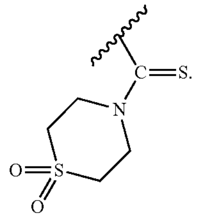 [SMILES: *C(=S)N1CCS(=O)(=O)CC1]

In embodiments of the compound of Formula I, the heterocyclic bases represented by Q may be selected from the naturally occurring purine and pyrimidine bases, e.g., adenine (A), cytosine (C), guanine (G), or modified purine and pyrimidine bases, and common analogs, e.g., such as are recited herein. Preferably, Q is selected from G and C, more preferably, Q is G.

In some embodiments, the heterocycle is selected from 1-methyladenine, 2-methyladenine, 8-bromoadenine, 2-thiocytosine, 3-methylcytosine, 5-methylcytosine, 5-ethylcytosine, 1-methylguanine, 2-methylguanine, 7-methylguanine, 8-bromoguanine, 8-chloroguanine, 8-aminoguanine, 8-methylguanine, 8-thioguanine, queosine, inosine, 1-methylinosine, hypoxanthine, xanthine, 2-aminopurine, 6-hydroxyaminopurine, 6-thiopurine and 2,6-diaminopurine.

In certain embodiments of the compound, the compound includes guanine as the heterocycle base and has the structure of Formula Ia:

Formula Ia

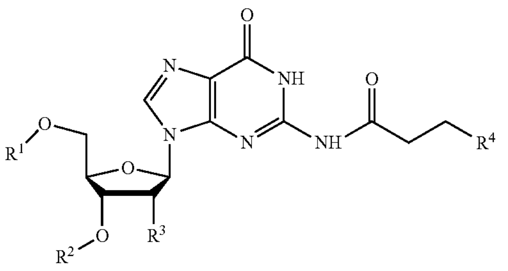

wherein each of $R^1$ or $R^2$ is independently selected from the group consisting of hydrogen, a protecting group, and a phosphoramidite group;

wherein $R^3$ is selected from the group consisting of H, F, O—$C_{1-6}$ alkyl, O-MOE, and a hydroxyl-removable protecting group; and wherein $R^4$ is a cyclic hydrocarbon.

In certain other embodiments, the compound includes cytosine as the heterocycle base and has the structure of Formula Ib:

Formula Ib

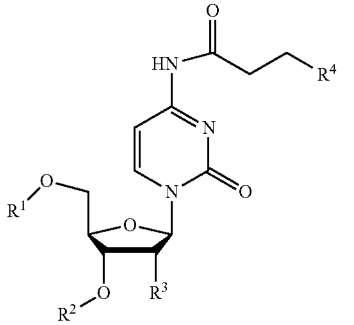

wherein each of $R^1$ or $R^2$ is independently selected from the group consisting of hydrogen, a protecting group, and a phosphoramidite group;

wherein $R^3$ is selected from the group consisting of H, F, O—$C_{1-6}$ alkyl, O-MOE, and a hydroxyl-removable protecting group; and wherein $R^4$ is a cyclic hydrocarbon.

In embodiments of the compound represented by Formula I, Ia, or Ib, the cyclic hydrocarbon has 3 to 10 carbon atoms or 5 to 6 carbon atoms. In certain embodiments, the cyclic hydrocarbon is cyclopentyl, cyclohexyl, or phenyl. In certain embodiments, the cyclic hydrocarbon is cyclopentyl.

In embodiments of the compound represented by Formula I, Ia, or Ib, $R^1$ or $R^2$ is each selected from, H, a protecting group and a phosphoramidite group. Typically, the protecting group is 4,4'-dimethoxytrityl (DMT) and the phosphoramidite group is 2-cyanoethyl-(N,N-diisopropylamine)-phosphoramidite or methyl-(N,N-diisopropylamine)-phosphoramidite.

Another aspect includes a method of synthesizing a nucleic acid comprising: contacting a nucleoside residue comprising a 5' (or 3') unprotected hydroxyl with a protected nucleotide monomer having the structure of Formula I:

Formula I

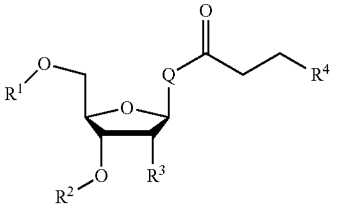

wherein each of $R^1$ or $R^2$ is independently selected from the group consisting of a protecting group, and a phosphoramidite group;

wherein $R^3$ is H, F, O—$C_{1-6}$ alkyl, O-MOE, or a O-thiocarbon protecting group;

wherein Q is a heterocyclic base; and wherein $R^4$ is a cyclic hydrocarbon under conditions sufficient to covalently bond said phosphoramidite group of the protected nucleotide monomer to said unprotected hydroxyl group of said nucleoside residue and produce an internucleotide bond.

In certain embodiments, the method further comprises exposing said internucleotide bond to an oxidizing agent. In certain embodiments, the method further comprises removing said 2'-hydroxyl protecting group. In certain embodiments, said nucleoside residue is covalently bound to a solid support. In particular embodiments, the method further comprises cleaving said nucleic acid from said solid support to produce a free nucleic acid.

Examples of the O-thiocarbon protecting group include, but are not limited to, thiocarbonates, thionocarbonates, and thionocarbamates. Embodiments of these compounds include compounds of the following structures:

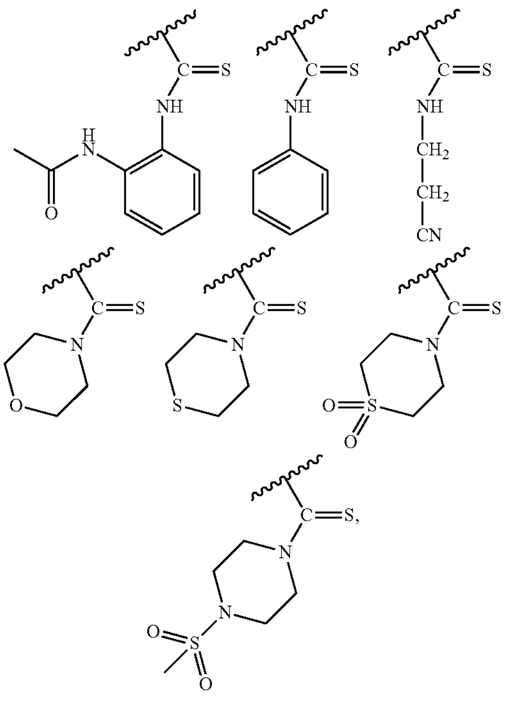

wherein the wiggly line indicates the point of attachment of the thionocarbamate group to the oxygen on the 2' carbon of the nucleotide. In certain embodiments, the O-thiocarbon protecting group is TC:

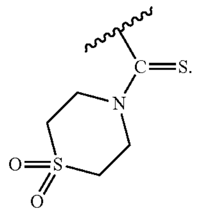 [SMILES: *C(=S)N1CCS(=O)(=O)CC1]

In certain embodiments of the method, the group R' or $R^2$ of the compound of Formula I, is each selected from a protecting group and a phosphoramidite group. Typically, the protecting group is 4,4'-dimethoxytrityl (DMT) and the phosphoramidite group is 2-cyanoethyl-(N,N-diisopropylamine)-phosphoramidite or methyl-(N,N-diisopropylamine)-phosphoramidite.

In embodiments of the compound of Formula I, the heterocyclic bases represented by Q may be selected from the naturally occurring purine and pyrimidine bases, e.g., adenine (A), cytosine (C), guanine (G), or modified purine and pyrimidine bases, and common analogs, e.g., such as are recited herein. Preferably, Q is selected from G and C, more preferably Q is G.

In some embodiments, the heterocycle is selected from 1-methyladenine, 2-methyladenine, 8-bromoadenine, 2-thiocytosine, 3-methylcytosine, 5-methylcytosine, 5-ethylcytosine, 1-methylguanine, 2-methylguanine, 7-methylguanine, 8-bromoguanine, 8-chloroguanine, 8-aminoguanine, 8-methylguanine, 8-thioguanine, queosine, inosine, 1-methylinosine, hypoxanthine, xanthine, 2-aminopurine, 6-hydroxyaminopurine, 6-thiopurine and 2,6-diaminopurine.

In certain embodiments of the compound represented by Formula I, the cyclic hydrocarbon has 3 to 10 carbon atoms or 5 to 6 carbon atoms. In certain embodiments, the cyclic hydrocarbon is cyclopentyl, cyclohexyl, or phenyl. In certain embodiments, the cyclic hydrocarbon is cyclopentyl.

Another aspect includes a nucleic acid comprising the structure:

FORMULA VIII

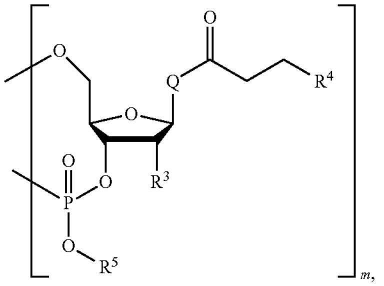

wherein $R^3$ is selected from H, F, O—$C_{1-6}$ alkyl, O-MOE, and a hydroxyl-removable protecting group;

wherein Q is a heterocyclic base;

wherein $R^4$ is a cyclic hydrocarbon;

wherein $R^5$ is selected from the group consisting of hydrogen, a hydrocarbyl, a substituted hydrocarbyl, an aryl, and a substituted aryl; and wherein m is an integer of at least 1.

In embodiments of the nucleic acid compounds, $R^3$ is H, F, O—$C_{1-6}$ alkyl, O-MOE, or a hydroxyl-removable protecting group. An example of an O—$C_{1-6}$ alkyl group is O—$CH_3$. An example of the hydroxyl-removable protecting group is a thiocarbon protecting group. Examples of the O-thiocarbon protecting group include, but are not limited to, thiocarbonates, thionocarbonates, and thionocarbamates. Embodiments of these compounds include compounds of the following structures:

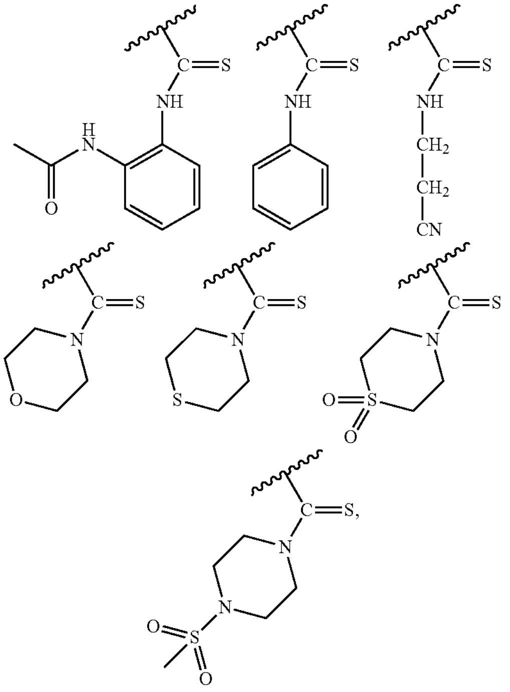

wherein the wiggly line indicates the point of attachment of the thionocarbamate group to the oxygen on the 2' carbon of the nucleotide. In certain embodiments, the 0-thiocarbon protecting group is TC:

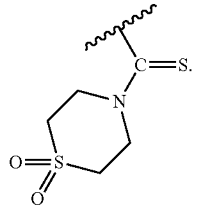 [SMILES: *C(=S)N1CCS(=O)(=O)CC1]

In embodiments of the nucleic acid compounds, the heterocyclic bases represented by Q may be selected from the naturally occurring purine and pyrimidine bases, e.g., adenine (A), cytosine (C), guanine (G), or modified purine and pyrimidine bases, and common analogs, e.g., such as are recited herein. Preferably, Q is selected from G and C, more preferably, Q is G.

In some embodiments, the heterocycle is selected from 1-methyladenine, 2-methyladenine, 8-bromoadenine, 2-thiocytosine, 3-methylcytosine, 5-methylcytosine, 5-ethylcytosine, 1-methylguanine, 2-methylguanine, 7-methylguanine, 8-bromoguanine, 8-chloroguanine, 8-aminoguanine, 8-methylguanine, 8-thioguanine, 5 queosine, inosine, 1-methylinosine, hypoxanthine, xanthine, 2-aminopurine, 6-hydroxyaminopurine, 6-thiopurine and 2,6-diaminopurine.

In certain embodiments of the nucleic acid compounds, the cyclic hydrocarbon represented by $R^4$ has 3 to 10 carbon atoms or 5 to 6 carbon atoms. In certain embodiments, the cyclic hydrocarbon is cyclopentyl, cyclohexyl, or phenyl. In certain embodiments, the cyclic hydrocarbon is cyclopentyl.

In certain embodiments of the nucleic acid compounds, $R^5$ is selected from the group consisting of hydrogen, a hydrocarbyl, a substituted hydrocarbyl, an aryl, and a substituted aryl. In certain embodiments, $R^5$ is selected from the group consisting of hydrogen, a hydrocarbyl, and a substituted hydrocarbyl. In certain embodiments, $R^5$ is selected from the group consisting of methyl and 2-cyanoethyl.

The foregoing and other features of the invention and advantages of the present invention will become more apparent in light of the following detailed description of particular embodiments, as illustrated in the accompanying figures. As will be realized, the invention is capable of modifications in various respects, all without departing from the invention. Accordingly, the drawings and the description are to be regarded as illustrative in nature, and not as restrictive.

BRIEF DESCRIPTION OF THE DRAWINGS

FIG. 2 is a UV-HPLC Chromatogram series showing deprotection products from 100mer rG(hcin)-RNA and rG(ibu)-RNA. The RNA deprotection reactions were performed with neat EDA at room temperature for 1 h 45 or at 40° C. for an hour.

FIG. 3 is a UV-HPLC Chromatogram series of a deprotection time course of Short RNA sequences (20mer) containing five rG(cpp) or rG(iBu). The RNAs were deprotected with neat EDA at 40° C. for a range of durations (30-75 min). FLP means "Full Length Product".

FIG. 4 is a picture of two ESI mass spectrometry scans overlays showing mass profiles of a 100mer RNA synthesized with rG(cpp) or rG(iBu) monomers. The 100mer RNAs were deprotected with neat EDA at 40° C. for a range of durations (30-90 min for rG(cpp)-RNA and 60-150 min for rG(ibu)-RNA). The complete deprotection of rG(cpp)-RNA and rG(ibu)-RNA were achieved at 75 min and 120 min respectively. FLP means "Full Length Product".

FIG. 5 is a UV-HPLC Chromatograms overlay of a 100mer rG(cpp)-RNA and a 100mer rG(ibu)-RNA deprotected with neat EDA at 40° C. for 60 min and 150 min respectively. The zoomed-in view of the overlayed chromatograms displays the significant differences in the amounts of shortmer byproducts obtained in these two deprotection reactions emphasizing the negative effect of a long deprotection time and its impact on the % FLP obtained respectively.

FIG. 6 is a ESI mass spectrometry scans overlays showing mass profiles of a 100mer RNA deprotection products (rG(cpp)-RNA and a 100mer rG(ibu)-RNA) obtained with neat EDA at 40° C. for 60 min and 150 min respectively. The overlay emphasizes the significant differences in the amount of depyrimidination impurities obtained in both cases.

DEFINITIONS

Figure 1:
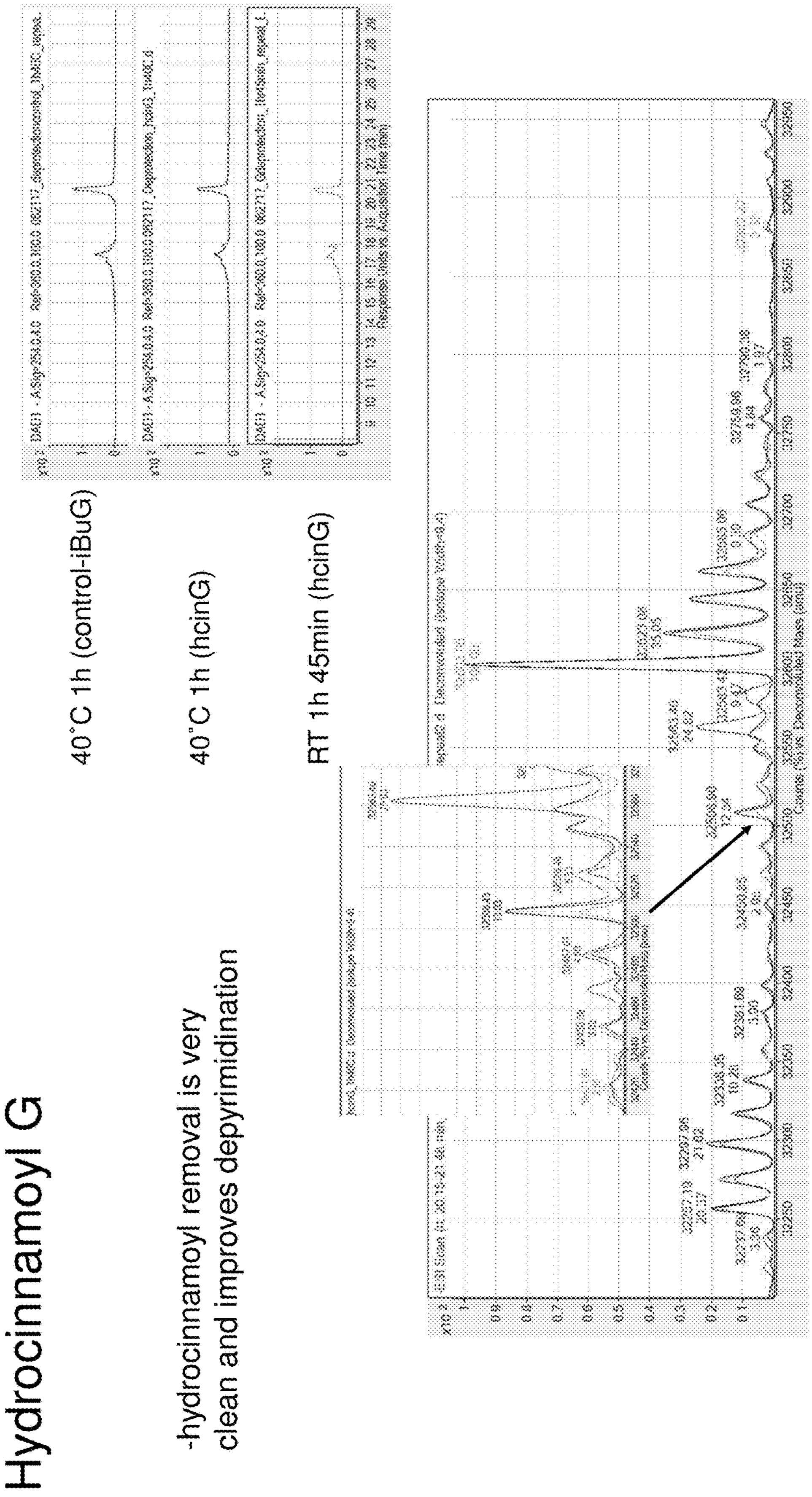
FIG. 1 is a ESI mass spectrometry scans overlay showing mass profiles of a 100mer RNA deprotection products synthesized either with $N^2$-hydrocinnamoyl guanosine rG(hcin) or with $N^2$-isobutyryl guanosine rG(ibu) monomers. The deprotection reactions are performed with neat EDA at room temperature for rG(hcin)-RNA for 1 h 45 or at 40° C. for an hour for rG(hcin)-RNA and rG(ibu)-RNA. The overlay of the Mass spectrometry scans shows that the hydrocinnamoyl removal at room temperature is very clean and decreases depyrimidination byproduct.

Prior to describing the invention in further detail, the terms used in this application are defined as follows unless otherwise indicated.

A "nucleotide" or "nucleotide moiety" refers to a sub-unit of a nucleic acid (whether DNA or RNA or analogue thereof) which includes a phosphate group, a sugar group and a heterocyclic base, as well as analogs of such sub-units. Other groups (e.g., protecting groups) can be attached to any component(s) of a nucleotide.

A "nucleoside" or "nucleoside moiety" references a nucleic acid subunit including a sugar group and a heterocyclic base, as well as analogs of such sub-units. Other groups (e.g., protecting groups) can be attached to any component(s) of a nucleoside.

A "nucleoside residue" refers to a molecule having a sugar group and a nitrogen containing base (as in a nucleoside) as a portion of a larger molecule, such as in a polynucleotide, oligonucleotide, or nucleoside phosphoramidite.

A "nucleotide monomer" refers to a molecule which is not incorporated in a larger oligo- or poly-nucleotide chain and which corresponds to a single nucleotide sub-unit; nucleotide monomers may also have activating or protecting groups, if such groups are necessary for the intended use of the nucleotide monomer.

The terms "nucleoside" and "nucleotide" are intended to include those moieties that contain not only the known purine and pyrimidine bases, e.g. adenine (A), thymine (T), cytosine (C), guanine (G), or uracil (U), but also other heterocyclic bases that have been modified. Such modifications include methylated purines or pyrimidines, acylated purines or pyrimidines, alkylated riboses or other heterocycles. Such modifications include, e.g., diaminopurine and its derivatives, inosine and its derivatives, alkylated purines or pyrimidines, acylated purines or pyrimidines thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, dimethylformamidine, dibutylformamidine, N,N-diphenyl carbamate, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides incorporating non-natural (not usually occurring in nature) nucleotides, unnatural nucleotide mimetics such as 2% modified nucleosides, peptide nucleic acids, oligomeric nucleoside phosphonates, and any polynucleotide that has added substituent groups, such as protecting groups or linking groups.

An "internucleotide bond" or "nucleotide bond" refers to a chemical linkage between two nucleoside moieties, such as the phosphodiester linkage in nucleic acids found in nature, or linkages well known from the art of synthesis of nucleic acids and nucleic acid analogues. An internucleotide bond may include a phospho or phosphite group, and may include linkages where one or more oxygen atoms of the phospho or phosphite group are either modified with a substituent or replaced with another atom, e.g., a sulfur atom, or the nitrogen atom of a mono- or di-alkyl amino group.

A "group" includes both substituted and unsubstituted forms. Substituents of interest include one or more lower alkyl, amino, imino, amido, alkylamino, arylamino, alkoxy, aryloxy, thio, alkylthio, arylthio, or aryl, or alkyl; aryl, alkoxy, thioalkyl, hydroxyl, amino, amido, sulfonyl, thio, mercapto, imino, halo, cyano, nitro, nitroso, azido, carboxy, sulfide, sulfone, sulfoxy, phosphoryl, silyl, silyloxy, and boronyl, or optionally substituted on one or more available carbon atoms with a nonhydrocarbyl substituent such as cyano, nitro, halogen, hydroxyl, sulfonic acid, sulfate, phosphonic acid, phosphate, phosphonate, or the like. Any substituents are chosen so as not to substantially adversely affect reaction yield (for example, not lower it by more than 20% (or 10%, or 5%, or 1%) of the yield otherwise obtained without a particular substituent or substituent combination). Further, substituents are chosen so as to be chemically compatible with the other groups present and to avoid side reactions known to those skilled in the art. For example, an alcohol would not be substituted with a lithium group, as the hydroxide of the alcohol and the lithium group are incompatible and would react with each other. For any group in this disclosure, each substituent may include up to 40, 35, 30, 25, 20, 18, 16, 14, 12, 11, 10, 9, 8, 7, 6, 5, 4 or 3 carbon atoms. Overall, the total number of carbon atoms in all the substituents for any group is, in certain embodiments, 80, 75, 70, 65, 60, 55, 50, 45, 40, 35, 30, 25, 20, 18, 16, 14, 12, 11, 10, 9, 8, 7, 6, 5, 4 or 3 or less.

The term "heterocycle", "heterocyclic", "heterocyclic group" or "heterocyclo" refers to fully saturated or partially or completely unsaturated cyclic groups having at least one heteroatom in at least one carbon atom-containing ring, including aromatic ("heteroaryl") or nonaromatic (for example, 3 to 13 member monocyclic, 7 to 17 member bicyclic, or 10 to 20 member tricyclic ring systems). Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be fused, bridged and/or joined through one or more spiro unions. Nitrogen-containing bases are examples of heterocycles. Other examples include piperidinyl, morpholinyl and pyrrolidinyl.

The terms "substituted heterocycle", "substituted heterocyclic", "substituted heterocyclic group" and "substituted heterocyclo" refer to heterocycle, heterocyclic, and heterocyclo groups substituted with one or more groups preferably selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, and the like, where optionally one or more pair of substituents together with the atoms to which they are bonded form a 3 to 7 member ring.

The term "electron-withdrawing group" refers to a moiety that has a tendency to attract valence electrons from neighboring atoms (i.e., the substituent is electronegative with respect to neighboring atoms). A quantification of the level of electron-withdrawing capability is given by the Hammett sigma constant. This well known constant is described in many references, for instance, March, Advanced Organic Chemistry 251-59, McGraw Hill Book Company, New York, (1977). Electron-withdrawing groups include nitro, acyl, formyl, sulfonyl, trifluoromethyl, cyano, chloride, and the like.

The term "electron-donating group" refers to a moiety that has a tendency to repel valence electrons from neighboring atoms (i.e., the substituent is less electronegative with respect to neighboring atoms). Electron-donating groups include amino, methoxy, alkyl (including C1-6 alkyl that can have a linear or branched structure), C4-9 cycloalkyl, and the like.

The phrase "protecting group" as used herein refers to a species which prevents a portion of a molecule from undergoing a specific chemical reaction, but which is removable from the molecule following completion of that reaction. A "protecting group" is used in the conventional chemical sense as a group which reversibly renders unreactive a functional group under certain conditions of a desired reaction, as taught, for example, in Greene, et al., "Protective Groups in Organic Synthesis," John Wiley and Sons, Second Edition, 1991. After the desired reaction, protecting groups may be removed to deprotect the protected functional group. All protecting groups should be removable (and hence, labile) under conditions which do not degrade a substantial proportion of the molecules being synthesized. In contrast to a protecting group, a "capping group" permanently binds to a segment of a molecule to prevent any further chemical transformation of that segment. It should be noted that the functionality protected by the protecting group may or may not be a part of what is referred to as the protecting group.

A "hydroxyl protecting group" or "0-protecting group" refers to a protecting group where the protected group is a hydroxyl. A "reactive-site hydroxyl" is the terminal 5'-hydroxyl during 3'-5' polynucleotide synthesis, or the 3'-hydroxyl during 5'-3' polynucleotide synthesis. A "free reactive-site hydroxyl" is a reactive-site hydroxyl that is available to react to form an internucleotide bond (e.g. with a phosphoramidite functional group) during polynucleotide synthesis.

A "thiocarbon protecting group" refers to a protecting group linked through a carbonyl or thionocarbonyl moiety which additionally has an oxygen, sulfur or nitrogen linked to one or more radicals independently selected from hydrogen, hydrocarbyls, and substituted hydrocarbyls with the proviso that when the thiocarbon protecting group is linked to the radical through a nitrogen, the radical can be additionally selected from aryls, substituted aryls, heterocycles or substituted heterocycles.

The term "deprotecting simultaneously" refers to a process which aims at removing different protecting groups in the same process and performed substantially concurrently or concurrently. However, as used herein, this term does not imply that the deprotection of the different protecting groups occur at exactly the same time or with the same rate or same kinetics.

A "phospho" group includes a phosphodiester, phosphotriester, and H-phosphonate groups. In the case of either a phospho or phosphite group, a chemical moiety other than a substituted 5-membered furyl ring may be attached to 0 of the phospho or phosphite group which links between the furyl ring and the P atom.

The term "phosphoramidite group" refers to a group comprising the structure P)—($OR^{13}$)($NR^{14}R^{15}$), wherein each of $R^{13}$, $R^{14}$, and $R^{15}$ is independently a hydrocarbyl, substituted hydrocarbyl, heterocycle, substituted heterocycle, aryl or substituted aryl. In some embodiments, $R^{13}$, $R^{14}$, and $R^{15}$ may be selected from lower alkyls, lower aryls, and substituted lower alkyls and lower aryls (preferably substituted with structures containing up to 18, 16, 14, 12, 11, 10, 9, 8, 7, 6, 5, 4, 3 or 2 carbons). In some embodiments, $R^{13}$ is 2-cyanoethyl or methyl, and either or both of $R^{14}$ and $R^{15}$ is isopropyl. $R^{14}$ and $R^{15}$ can optionally be cyclically connected.

The term "alkyl" as used herein, unless otherwise specified, refers to a saturated straight chain, branched or cyclic hydrocarbon group of 1 to 24, typically 1-12, carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to six carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl.

Moreover, the term "alkyl" includes "modified alkyl", which references an alkyl group having from one to twenty-four carbon atoms, and further having additional groups, such as one or more linkages selected from ether-, thio-, amino-, phospho-, oxo-, ester-, and amido-, and/or being substituted with one or more additional groups including lower alkyl, aryl, alkoxy, thioalkyl, hydroxyl, amino, sulfonyl, thio, mercapto, imino, halo, cyano, nitro, nitroso, azide, carboxy, sulfide, sulfone, sulfoxy, phosphoryl, silyl, silyloxy, and boronyl. Similarly, the term "lower alkyl" includes "modified lower alkyl", which references a group having from one to six carbon atoms and further having additional groups, such as one or more linkages selected from ether-, thio-, phospho-, keto-, ester-, and amido-, and/or being substituted with one or more groups including lower alkyl; aryl, alkoxy, thioalkyl, hydroxyl, amino, sulfonyl, thio, mercapto, imino, halo, cyano, nitro, nitroso, azide, carboxy, sulfide, sulfone, sulfoxy, phosphoryl, silyl, silyloxy, and boronyl. The term "alkoxy" as used herein refers to a substituent —O—R wherein R is alkyl as defined above. The term "lower alkoxy" refers to such a group wherein R is lower alkyl. The term "thioalkyl" as used herein refers to a substituent —S—R wherein R is alkyl as defined above.

The term "alkenyl" as used herein, unless otherwise specified, refers to a branched, unbranched or cyclic (e.g. in the case of C5 and C6) hydrocarbon group of 2 to 24, typically 2 to 12, carbon atoms containing at least one double bond, such as ethenyl, vinyl, allyl, octenyl, decenyl, and the like. The term "lower alkenyl" intends an alkenyl group of two to eight carbon atoms, and specifically includes vinyl and allyl. The term "cycloalkenyl" refers to cyclic alkenyl groups.

The term "alkynyl" as used herein, unless otherwise specified, refers to a branched or unbranched hydrocarbon group of 2 to 24, typically 2 to 12, carbon atoms containing at least one triple bond, such as acetylenyl, ethynyl, n-propynyl, isopropynyl, n-butynyl, isobutynyl, t-butynyl, octynyl, decynyl and the like. The term "lower alkynyl" intends an alkynyl group of two to eight carbon atoms, and includes, for example, acetylenyl and propynyl, and the term "cycloalkynyl" refers to cyclic alkynyl groups.

The term "hydrocarbyl" refers to alkyl, alkenyl or alkynyl. The term "substituted hydrocarbyl" refers to hydrocarbyl moieties having substituents replacing a hydrogen on one or more carbons of the hydrocarbon backbone. Such substituents may include, for example, a hydroxyl, a halogen, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclic, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN, and the like. Cycloalkyls may be further substituted with alkyls, alkenyls, alkoxys, alkylthios, aminoalkyls, carbonyl-substituted alkyls, —CN, and the like.

The term "alkoxy" means an alkyl group linked to oxygen and may be represented by the formula: R—O—, wherein R represents the alkyl group. An example is the methoxy group $CH_3O$—.

The term "MOE" means methyloxyethyl or methyloxyethylene. A nucleoside with an MOE group is usually called a 2'-MOE nucleoside, in which the 2' carbon of the nucleoside (or nucleotide), is linked to a O—$CH_2CH_2O$—$CH_3$ group.

The term "aryl" refers to 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The term "aryl" also includes polycyclic ring systems having two or more cyclic rings in which two or more carbons are common to two adjoining rings (the rings are "fused rings") wherein at least one of the rings is aromatic (e.g., the other cyclic rings may be cycloalkyls, cycloalkenyls, cycloalkynyls, aryls, and/or heterocycles). A "lower aryl" contains up to 18 carbons, such as up to 14, 12, 10, 8 or 6 carbons.

The aromatic rings may be substituted at one or more ring positions with such substituents as described above for substituted hydrocarbyls, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclic, aromatic or heteroaromatic moieties, —$CF_3$, —CN, or the like.

The terms "halogen" and "halo" refer to fluorine (F), chlorine (Cl), bromine (Br), or iodine (I).

"Linkage" as used herein refers to a first moiety bonded to two other moieties, wherein the two other moieties are linked via the first moiety. Typical linkages include ether (—O—), oxo (—C(O)—), amino (—NH—), amido (—N—C(O)—), thio (—S—), phospho (—P—), ester (—O—C(O)—).

"Functionalized" references a process whereby a material is modified to have a specific moiety bound to the material, e.g. a molecule or substrate is modified to have the specific moiety; the material (e.g. molecule or support) that has been so modified is referred to as a functionalized material (e.g. functionalized molecule or functionalized support).

The term "substituted" as used to describe chemical structures, groups, or moieties, refers to the structure, group, or moiety comprising one or more substituents. As used herein, in cases in which a first group is "substituted with" a second group, the second group is attached to the first group whereby a moiety of the first group (typically a hydrogen) is replaced by the second group.

"Substituent" references a group that replaces another group in a chemical structure. Typical substituents include nonhydrogen atoms (e.g. halogens), functional groups (such as, but not limited to amino, sulfhydryl, carbonyl, hydroxyl, alkoxy, carboxyl, silyl, silyloxy, phosphate and the like), hydrocarbyl groups, and hydrocarbyl groups substituted with one or more heteroatoms. Exemplary substituents include alkyl, lower alkyl, aryl, aralkyl, lower alkoxy, thioalkyl, hydroxyl, thio, mercapto, amino, imino, halo, cyano, nitro, nitroso, azide, carboxy, sulfide, sulfone, sulfoxy, phosphoryl, silyl, silyloxy, boronyl, and modified lower alkyl.

Hyphens, or dashes are used at various points throughout this specification to indicate attachment, e.g. where two named groups are immediately adjacent to a dash in the text, this indicates that the two named groups area attached to each other. Similarly, a series of named groups with dashes between each of the named groups in the text indicated the named groups are attached to each other in the order shown. Also, a single named group adjacent a dash in the text indicates that the named group is typically attached to some other, unnamed group. In some embodiments, the attachment indicated by a dash may be, e.g., a covalent bond between the adjacent named groups. At various points throughout the specification, a group may be set forth in the text with or without an adjacent dash, (e.g. amido or amido-, further e.g. alkyl or alkyl-, yet further Lnk, Lnk- or -Lnk-) where the context indicates the group is intended to be (or has the potential to be) bound to another group; in such cases, the identity of the group is denoted by the group name (whether or not there is an adjacent dash in the text). Note that where context indicates, a single group may be attached to more than one other group (e.g., where a linkage is intended, such as linking groups).

Dashed lines (e.g., - - - - - -) are used throughout the specification adjacent to named groups to indicate attachment to some other, unnamed group.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present. At various points herein, a moiety may be described as being present zero or more times: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly. Similarly, a moiety may be described as being either (1) a group linking two adjacent groups, or (2) a bond linking the two adjacent groups: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly.

"Bound" may be used herein to indicate direct or indirect attachment. In the context of chemical structures, "bound" (or "bonded") may refer to the existence of a chemical bond directly joining two moieties or indirectly joining two moieties (e.g. via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect. "Free," as used in the context of a moiety that is free, indicates that the moiety is available to react with or be contacted by other components of the solution in which the moiety is a part.

The term "assessing" includes any form of measurement, and includes determining if an element is present or not. The terms "determining", "measuring", "evaluating", "assessing" and "assaying" are used interchangeably and may include quantitative and/or qualitative determinations. Assessing may be relative or absolute. "Assessing the presence of" includes determining the amount of something present and/or determining whether it is present or absent.

"Isolated" or "purified" generally refers to isolation of a substance (compound, polynucleotide, protein, polypeptide, polypeptide, chromosome, etc.) such that the substance comprises a substantial portion of the sample in which it resides (excluding solvents), i.e. greater than the substance is typically found in its natural or un-isolated state. Typically, a substantial portion of the sample comprises at least about 1%, at least about 5%, at least about 10%, at least about 20%, at least about 30%, at least about 50%, preferably at least about 80%, or more preferably at least about 90% of the sample (excluding solvents). For example, a sample of isolated RNA will typically comprise at least about 5% total RNA, where percent is calculated in this context as mass (e.g. in micrograms) of total RNA in the sample divided by mass (e.g. in micrograms) of the sum of (total RNA+other constituents in the sample (excluding solvent)). Techniques for purifying polynucleotides and polypeptides of interest are well known in the art and include, for example, gel electrophoresis, ion-exchange chromatography, affinity chromatography, flow sorting, and sedimentation according to density. In typical embodiments, one or more of the nucleotide composition(s) is in isolated form; more typically, all three are obtained in isolated form prior to use in the present methods.

The term "pre-determined" refers to an element whose identity is known prior to its use. For example, a "pre-determined sequence" is a sequence whose identity is known prior to the use or synthesis of the polynucleotide having the sequence. An element may be known by name, sequence, molecular weight, its function, or any other attribute or identifier.

"Upstream" as used herein refers to the 5' direction along a polynucleotide, e.g. an RNA molecule. "Downstream" refers to the 3' direction along the polynucleotide. "3'-" and "5'-" have their conventional meaning as known in the art.

DETAILED DESCRIPTION OF PARTICULAR EMBODIMENTS

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It should be noted that, as is conventional in drawing some chemical structures, some of the hydrido groups are omitted from the drawn structures for clarity purposes, but should be understood to be present, e.g. where necessary to completely fill out the valence bonding of a carbon in a drawn structure.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Exocyclic Amino Heterocycle Protected Nucleoside Monomers.

As summarized above, monomers are disclosed herein having an exocyclic amino heterocycle protecting group. In certain embodiments, the exocyclic amino heterocycle protecting group is a propanoyl having a terminal cyclic hydrocarbon.

Embodiments include nucleoside monomers as described by Formula (I):

Formula I

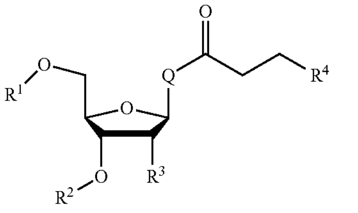

- wherein each of $R^1$ or $R^2$ is independently selected from the group consisting of hydrogen, a protecting group, and a phosphoramidite group;
- wherein $R^3$ is selected from the group consisting of H, F, O—$C_{1-6}$ alkyl, O-MOE and a hydroxyl-removable protecting group;
- wherein Q is a heterocyclic base; and
- wherein $R^4$ is selected from the group consisting of a cyclic hydrocarbon.

In certain embodiments, the nucleoside monomers are described by Formula (Ia):

Formula Ia

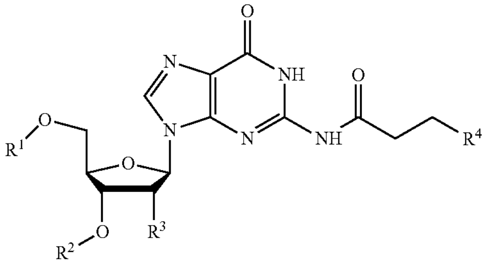

- wherein each of $R^1$ or $R^2$ is independently selected from the group consisting of hydrogen, a protecting group, and a phosphoramidite group;
- wherein $R^3$ is selected from the group consisting of H, F, O—$C_{1-6}$ alkyl, O-MOE and a hydroxyl-removable protecting group; and
- wherein $R^4$ is a cyclic hydrocarbon.

In certain other embodiments, the nucleoside monomers are described by Formula (Ib):

Formula Ib

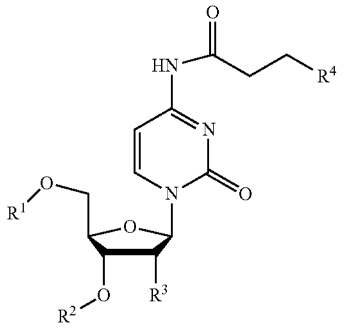

- wherein each of $R^1$ or $R^2$ is independently selected from the group consisting of hydrogen, a protecting group, and a phosphoramidite group;
- wherein $R^3$ is selected from the group consisting of H, F, O—$C_{1-6}$ alkyl, O-MOE and a hydroxyl-removable protecting group; and
- wherein $R^4$ is a cyclic hydrocarbon.

In each of the embodiments above, the terminal cyclic hydrocarbon may be a cycloalkyl, cycloalkenyl, cycloalkynyl, or aryl. In certain embodiments, the protective group is cycloalkylpropanoyl or arylpropoanoyl. In certain embodiments, the alkyl or aryl portions of the cycloalkylproanoyl or arylpropanoyl moieties have 3 to 10 carbon atoms, or 5 to 6 carbon atoms. In particular embodiments, the protective group is cyclopentylpropanoyl (cpp), cyclohexylpropanoyl, or hydrocinnamoyl (hyn). In other particular embodiments, the protective group is cyclopentylpropanoyl (cpp).

In embodiments of the compound represented by Formula I, Ia, or Ib, $R^1$ or $R^2$ is each selected from, H, a protecting group and a phosphoramidite group. Typically, the protecting group is 4,4'-dimethoxytrityl (DMT) and the phosphoramidite group is 2-cyanoethyl-(N,N-diisopropyl amine)-phosphoramidite or methyl-(N,N-diisopropylamine)-phosphoramidite.

In certain embodiments of the compound represented by Formula I, Ia, or Ib, $R^3$ is a hydroxyl-removable protecting group. An example of the removable protecting group is a O-thiocarbon protecting group. Examples of the O-thiocarbon protecting group include, but are not limited to, thiocarbonates, thionocarbonates, and thionocarbamates. Embodiments of these compounds include compounds of the following structures:

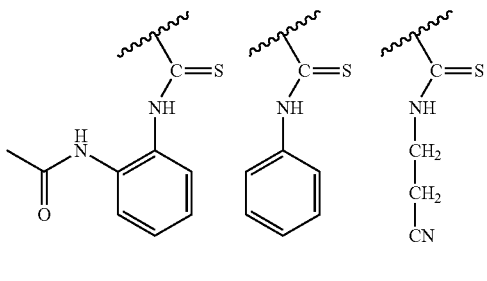

-continued

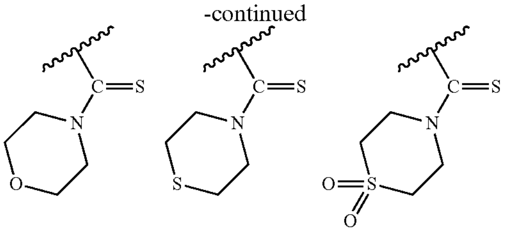

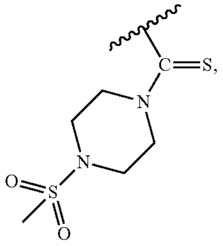

wherein the wiggly line indicates the point of attachment of the thionocarbamate group to the oxygen on the 2' carbon of the nucleotide. In certain embodiments, the O-thiocarbon protecting group is TC:

TC

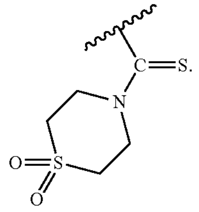

In embodiments of the compound of Formula I, Ia, or Ib, the heterocyclic bases represented by Q may be selected from the naturally occurring purine and pyrimidine bases, e.g., adenine (A), cytosine (C), guanine (G), or modified purine and pyrimidine bases, and common analogs, e.g., such as are recited herein. Preferably, Q is selected from G and C, more preferably, Q is G.

In some embodiments, the heterocycle is selected from 1-methyladenine, 2-methyladenine, 8-bromoadenine, 2-thiocytosine, 3-methylcytosine, 5-methylcytosine, 5-ethylcytosine, 1-methylguanine, 2-methylguanine, 7-methylguanine, 8-bromoguanine, 8-chloroguanine, 8-aminoguanine, 8-methylguanine, 8-thioguanine, queosine, inosine, 1-methylinosine, hypoxanthine, xanthine, 2-aminopurine, 6-hydroxyaminopurine, 6-thiopurine and 2,6-diaminopurine.

Synthesis of Exocyclic Amino Heterocycle Protected Nucleoside Monomers.

The nucleoside monomers having a protected heterocycle base can be produced using any convenient protocol. In certain embodiments, the protected nucleoside monomers are produced using a protocol in which a nucleoside monomer having the structure shown in Formula (II):

Formula II

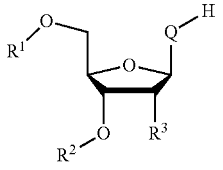

wherein each of $R^1$ or $R^2$ is independently selected from a hydrogen and a protecting group;

wherein $R^3$ is selected from the group consisting of H, OH, F, O—$C_{1-6}$ alkyl, O-MOE and a hydroxyl-removable protecting group; when $R^3$ is a O-protecting group, R', $R^2$ and $R^3$ can be the same or different; and wherein Q is a heterocyclic base;

is contacted with a compound having the structure $R^4$—$C_2H_4$CO-LG, wherein $R^4$ is selected from cycloalkyl, cycloalkenyl, cycloalkynyl, or aryl, and wherein LG is a leaving group, such as a halo group;

under conditions sufficient to produce a protected nucleoside monomer of the structure of Formula (I).

Examples of leaving or activating groups suitable for LG include, but are not limited to, imidazole, chloro, p-nitrophenoxy, pentafluoro phenoxy, 0-succinimidyl, trichloromethyl, bromo, and iodo.

N-3-(cycloalkyl)propanoyl nucleoside derivatives of this invention were prepared using procedures modified from the Jones's transient silylation protocol *Organic Letters,* 2004 Vol. 6 No. 15; 2555-2557. The nucleoside is first transiently silylated on the $O^6$, and $N^2$-guanine positions, (or the $N^4$-cytosine or $N^6$-adenine positions) and the 2', 3' and 5' hydroxyl positions of the ribose with trimethylsilyl chloride, and in a second step reacted with the desired acyl chloride to yield the N-3-(cycloalkyl)propanoyl-protected respective amino positions of the heterocycles of the nucleosides (as for example, depicted in compounds 1A, 1B, 1C).

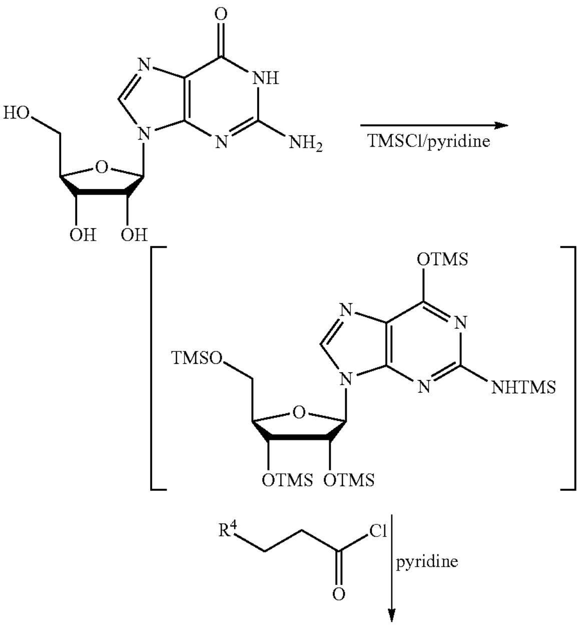

-continued

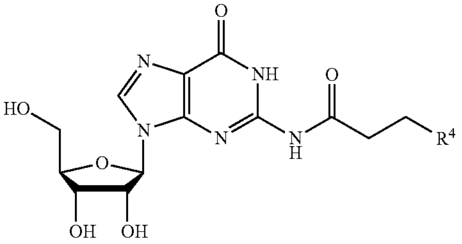

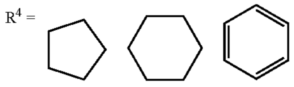

1A , 1B , 1C

In certain embodiments, as illustrated below, the synthesis of the corresponding phosphoramidite monomers may follow with the use of a Markiewicz 1,1,3,3-tetraisopropyldisiloxane (TIPS) reagent to localize protecting groups to the 2'-OH site of the composition under synthesis, i.e., to provide regioselectivity. A regiospecific introduction on the 2'-hydroxyl protecting group is performed through the protection of the 5' and 3'-hydroxyl groups, e.g., through the use of a Markiewicz 1,1,3,3-tetraisopropyldisilyloxane protecting group (Markiewicz W. T., *J. Chem. Research* (S), 1979, 24-25) as shown in the structure of formula (III) below.

Formula (III)

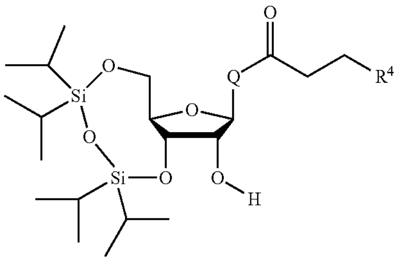

wherein $R^4$ is selected from cycloalkyl, cycloalkenyl, cycloalkynyl, or aryl.

Some embodiments involve the synthesis of 2'-thionocarbamates, wherein a 3',5'-disiloxane protected nucleoside of Formula (III) can be reacted with 1,1'-thiocarbonyldiimidazole in acetonitrile in the presence of a catalytic amount of 4-(dimethyl)aminopyridine (DMAP). The reaction described above may result in a quantitative, for example at least, 90%, at least 95%, at least 98%, at least 99%, at least 99.5% or at least 99.9% conversion of the protected nucleoside to the imidazole thionocarbamate having a structure of Formula IV and may give a crystalline product.

Formula IV

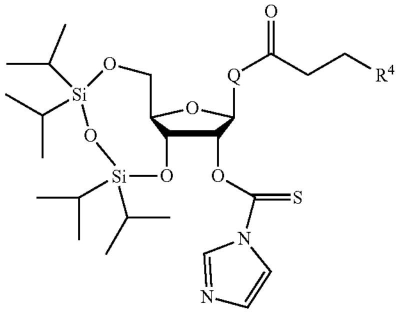

wherein $R^4$ is selected from cycloalkyl, cycloalkenyl, cycloalkynyl, or aryl.

Disclosed herein is the reaction of a compound of Formula IV with 1.1 equivalents of ammonia, a primary, or a secondary amine in acetonitrile with a catalytic amount of 4-(dimethyl)aminopyridine; wherein the reaction may result in a quantitative or near quantitative conversion, for example at least 90%, at least 95%, at least 98% or at least 99% conversion to the 2'-thionocarbamate derivative. In the case of aniline or other weak nucleophiles, one equivalent of 4-(dimethyl)aminopyridine (DMAP) may be used to achieve complete conversion to the corresponding thionocarbamate derivative. In the case of weak nucleophiles that are sterically constrained, such as dicyanoethylamine, the reaction may employ refluxing conditions in acetonitrile, overnight, with one equivalent of 4-(dimethyl)aminopyridine and the resulting product may be isolated in 70% yield. In the case of the thiomorpholine 1,1-dioxide that is used to synthesize the 2'-O-(1,1-dioxo-1$\lambda^6$-thiomorpholine-4-carbothioate) nucleosides as shown in Formula V, known as 2'-O-TC nucleosides, the addition of the amine may be performed immediately after obtaining the 2'-imidazole thionocarbamate intermediate (Formula IV) without having to isolate it.

Formula V

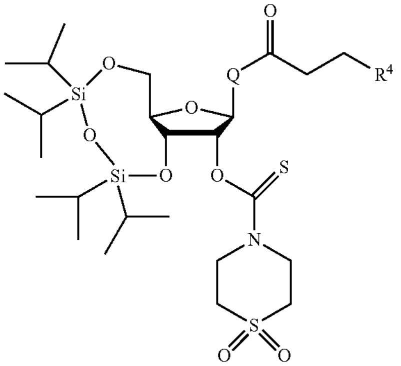

wherein $R^4$ is selected from cycloalkyl, cycloalkenyl, cycloalkynyl, or aryl. Embodiments of 2'-thionocarbamate compounds of Formula V include compounds with the following 2'-protecting group structures:

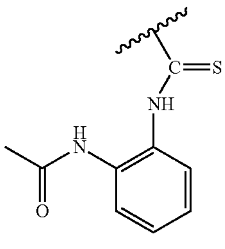
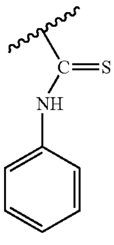
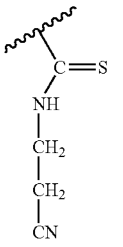

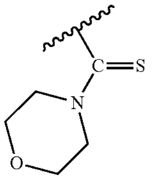
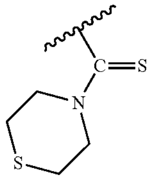
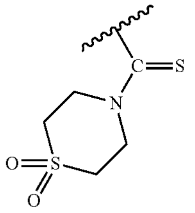

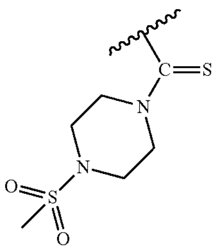

wherein the wiggly line indicates the point of attachment of the thionocarbamate group to the oxygen on the 2' carbon of the nucleoside.

Also disclosed herein is the protection of 5' (or 3')-hydroxyl, followed by 3' (or 5') phosphitylation. The 3',5'-tetraisopropyldisiloxane-2'-thionocarbamate protected nucleoside (Formula V) may be converted to active RNA synthesis monomers in three more synthetic steps by first removing the 3',5'-tetraisopropyldisiloxane protecting group with 15 eq. to 40 eq. of HF/pyridine to produce the 2'-thionocarbamate-ribonucleoside intermediate. This intermediate may then be reacted with 4,4'-dimethoxytrityl chloride (DMTrCl) with 5 eq. to 10 eq. of collidine or N-methylimidazole (NMI) to produce a 5'-O-dimethoxytrityl(DMT)-2'-thionocarbamate-ribonucleoside derivative; that product may then be reacted with a phosphytilating reagent such as chloro(diisopropylamino)-2-cyanoethoxyphosphine ($NC—CH_2—CH_2—O—P(Cl)—N(iPr)_2$), or bis(diisopropylamino)(2-cyanoethoxy)phosphine ($NC—CH_2—CH_2—O—P—[N(iPr)_2]_2$), or chloro(diisopropylamino) methoxyphosphine ($CH_3—O—P(Cl)—N(iPr)_2$), or bis (diisopropylamino)methoxyphosphine ($CH_3—O—P—[N(iPr)_2]_2$), to produce a 5'-O-DMT-2'-thionocarbamate-ribonucleoside-3'-O-methyl(- or 2-cyanoethyl)(N,N diisopropyl)phosphoramidite compound of Formula VI.

Formula VI

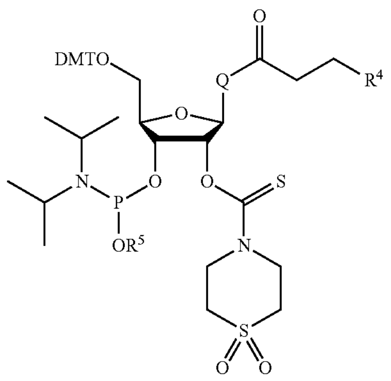

wherein $R^4$ is selected from cycloalkyl, cycloalkenyl, cycloalkynyl, or aryl and $R^5$ is selected from 2-cyanoethyl and methyl.

In some embodiments, wherein 5' to 3' oligonucleotide synthesis is desired, a modification of the method described above may be used to prepare a 3'-O-DMT-2'-thionocarbamate-ribonucleoside-5'-O-methyl(- or 2-cyanoethyl)(N,N-diisopropyl)phosphoramidite (for example by the following steps: a. protection with TIPS; b. 2'-thionocarbamate formation; c. removal of TIPS; d. phosphitylation of 5'OH; e. tritylation of 3'OH; or a. protection with TIPS; b. 2'-thionocarbamate formation; c. removal of TIPS d. protection of 5'-OH with TBDMS; e. tritylation of 3'-OH; f. removal of TBDMS; g. 5'-OH phosphitylation).

Nucleic Acid Synthesis Using Monomers with 2'-Thionocarbamate Protecting Groups.

In some embodiments, solid phase synthesis of oligoribonucleotides follows the same cycle as DNA synthesis. A solid support, typically Controlled Pore Glass (CPG) with an attached nucleoside is subjected to removal of the protecting group on the 5'-hydroxyl of the nucleoside. The incoming phosphoramidite is coupled to the growing chain in the presence of an activator. Any unreacted 5'-hydroxyl is capped and the phosphite triester internucleotide linkage produced in the coupling reaction is then oxidized to provide the desired phosphate triester linkage. The process is then repeated until an oligomer of the desired length results. The actual reagents used may vary depending on the 5'- and 2'-protecting groups. Other ancillary reagents may also differ.

In some embodiments the 2'-thionocarbamate nucleotide monomers described herein can be used to synthesize nucleic acids that comprise one or more ribonucleotide residues. The synthesis may be performed in either direction: from 3' to 5' or from 5' to 3'. For example, in the 3' to 5' direction, a first nucleoside monomer with a 5'-OH is coupled, in the presence of an activator (for example, tetrazole or S-ethylthio-tetrazole), with a nucleotide monomer having a 3'-phosphoramidite and a 5'-O-protecting group (typically DMT). The first nucleoside monomer is optionally bound to a solid support, for example through a succinimidyl linker on the 3'-hydroxyl. Alternatively, the synthesis can be performed in solution. After the coupling step, in which the 5'-OH and the 3'-phosphoramidite condense to form a phosphite triester linkage and result in a dinucleotide, the unreacted 5'-hydroxyls of the first nucleoside monomer may be optionally capped with acetic anhydride solution either prior to and/or after oxidation. During oxidation, the phosphite triester linkages are oxidized either with a solution containing iodine to obtain the phosphate triester or with a sulfurization agent, when a phosphorothioate linkage is desired. The 5'-DMT protecting group is then removed (deprotection) with an anhydrous acid solution; for example, 3% of trichloroacetic acid (TCA) in methylene chloride or 5%-10% dichloroacetic acid (DCA) in toluene. The newly formed dinucleotide is then ready for coupling with another nucleotide monomer having a 3'-phosphoramidite and a 5'-DMT protecting group. These steps may be repeated until the nucleic acid reaches the desired length and/or sequence.

In some embodiments, the 2'-thionocarbamate nucleotide monomers having a 3'-H-phosphonate as in the structure of formula VII can be used to synthesize nucleic acids, that comprise one or more ribonucleotide residues; where $R^1$ is a hydroxyl protecting group, Q is a heterocyclic base, $R^3$ is a thionocarbamate protecting group, and $R^4$ is a cyclic hydrocarbon.

Formula VII

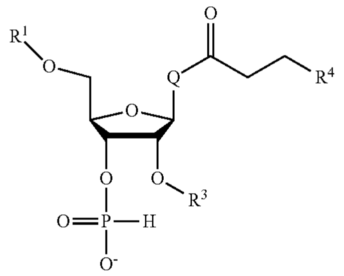

For example, in the 3' to 5' direction, a first nucleoside monomer with a 5'-OH is coupled, in the presence of an activator (for example, adamantane carbonyl chloride) with a nucleotide monomer having a 3'-H-phosphonate, a 2'-O-protecting group (typically TC) and a 5'-O-protecting group (typically DMT). The first nucleoside monomer is optionally bound to a solid support, for example through a succinimidyl linker on the 3'-hydroxyl. Alternatively, the synthesis can be performed in solution. After the coupling step, in which the 5'-OH and the 3'-H-phosphonate condense to form a H-phosphonate linkage and result in a dinucleotide, the unreacted 5'-hydroxyl groups of the first nucleoside monomer are capped with a capping reagent (such as, but not limited to, isopropyl phosphite in the presence of adamantane carbonyl chloride). The 5'-DMT protecting group is then removed (deprotection) with an anhydrous acid solution; for example, 3% of trichloroacetic acid (TCA) in methylene chloride, or 5%-10% dichloroacetic acid (DCA) in toluene. The newly formed dinucleotide is then ready for coupling with another nucleotide monomer having a 3'-H-phosphonate, a 2'-O-protecting group and a 5'-O-DMT protecting group. These steps may be repeated until the nucleic acid reaches the desired length and/or sequence. The fully protected oligonucleotide comprising at least one ribonucleotide is then reacted with an oxidizing solution comprising iodine and N-methylmorpholine to oxidize all at once all the H-phosphonate linkages into phosphodiester linkages or with a solution comprising a sulfurization reagent to produce all at once phosphorothioate linkages.

In some embodiments, thionocarbamate protections on the 2'-hydroxyl enable the synthesis of long sequences of RNA because of the ease and efficiency of the TC chemistry and the ease of removal of these protecting groups. The nucleic acids synthesized by some embodiments of the methods disclosed herein may be as long as 20, 25, 30, 35, 40, 45, 50, 55, 60, 65, 70, 75, 80, 85, 90, 95, 100, 105, 110, 115, 120, 125, 130, 135, 140, 145, 150, 200 or 500 nucleotides in length or longer. Furthermore, a nucleic acid synthesized according to some embodiments can be combined with another nucleic acid to form longer nucleic acids. For example, a nucleic acid of 70 bases can be coupled with another nucleic acid of 70 bases by chemical ligation, or other chemical reaction that results in a non-natural internucleotide linkage, such as for example, the use of click chemistry or squarate chemistry, known in the art to link two or more nucleic acids or to conjugate a non-oligonucleotide moiety such as for example but not limited to: lipid, peptide, cholesterol, vitamin, PEG, a dye to an oligonucleotide. As another example, two nucleic acids can be ligated with an RNA ligase wherein the 2'-protecting groups may be removed before ligation.

The synthetic methods described herein may be conducted on a solid support having a surface to which chemical entities may bind. In some embodiments, multiple oligonucleotides being synthesized are attached, directly or indirectly, to the same solid support and may form part of an array. An "array" is a collection of separate molecules of known monomeric sequence each arranged in a spatially defined and a physically addressable manner, such that the location of each sequence is known. The number of molecules, or "features," that can be contained on an array will largely be determined by the surface area of the substrate, the size of a feature and the spacing between features, wherein the array surface may or may not comprise a local background region represented by non-feature area. Arrays can have densities of up to several hundred thousand or more features per $cm^2$, such as 2,500 to 200,000 features/$cm^2$. The features may or may not be covalently bonded to the substrate. An "array," or "chemical array" used interchangeably includes any one-dimensional, two-dimensional or substantially two-dimensional (as well as a three-dimensional) arrangement of addressable regions bearing a particular chemical moiety or moieties (such as ligands, e.g., biopolymers such as polynucleotide or oligonucleotide sequences (nucleic acids), polypeptides (e.g., proteins), carbohydrates, lipids, etc.) associated with that region. An array is "addressable" when it has multiple regions of different moieties (e.g., different polynucleotide sequences) such that a region (i.e., a "feature" or "spot" or "well" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "probe" may be the one which is to be evaluated by the other (thus, either one could be an unknown mixture of analytes, e.g., polynucleotides, to be evaluated by binding with the other).

An array of polynucleotides, as described herein, may include a two or three-dimensional array of beads. In certain cases, the beads are linked to an oligonucleotide that has two portions, a first portion that binds to a target, and a second portion that contains a nucleotide sequence that identifies the oligonucleotide. In other cases, the bead may provide an optical address for the oligonucleotide, thereby allowing the identity of the oligonucleotide to be determined.

In one embodiment, the array may be in the form of a 3-dimensional multiwell array such as the Illumina BeadChip. One embodiment of BeadChip technology is the attachment of oligonucleotides to silica beads. The beads are then randomly deposited into wells on a substrate (for example, a glass slide). The resultant array is decoded to determine which oligonucleotide-bead combination is in which well. The decoded arrays may be used for a number of applications, including gene expression analysis and genotyping. Gene expression analysis may be performed using, for example, a 50-200 oligonucleotide that has two segments. For example, a 50-150 base segment at one end of the oligonucleotide may be designed to hybridize to a labeled target sequence. The other end of the oligonucleotide may serve as the address. The address is a unique sequence to allow unambiguous identification of the oligonucleotide after it has been deposited on the array. Bead Arrays may have, for example, 1,000 to 1,000,000 or more unique oligonucleotides. Each oligonucleotide may be synthesized in a large batch using standard technologies. The oligonucleotides may then be attached to the surface of a silica bead, for example a 1-5-micron bead. Each bead may have only one type of oligonucleotide attached to it, but have hundreds of thousands of copies of the oligonucleotide. Standard lithographic techniques may be used to create a honeycomb pattern of wells on the surface, for example a glass slide. Each well may hold a bead. The beads for a given array may be mixed in equal amounts and deposited on the slide surface, to occupy the wells in a random distribution. Each bead may be represented by, for example, about 20 instances within the array. The identity of each bead may be determined by decoding using the address sequence. A unique array layout file may then associated with each array and used to decode the data during scanning of the array.

With the efficiency and ease of some methods described herein, oligonucleotide, comprising at least one ribonucleotide, synthesis can be performed in small or large scales. The quantity of oligonucleotide made in one complete run of a particular method (in one container) can thus be less than a microgram, or in micrograms, tens of micrograms, hundreds of micrograms, grams, tens of grams, hundreds of grams, or even kilograms.

As such, some embodiments described herein include methods of synthesizing nucleic acids that comprise the steps of providing a nucleotide residue or a nucleoside monomer having an unprotected hydroxyl group; and a nucleotide monomer with a 2'-thionocarbamate protecting group; and contacting the nucleotide residue or nucleoside monomer with the 2'-thionocarbamate protected nucleotide monomer under conditions sufficient to covalently bond the 2'-thionocarbamate protected nucleotide monomer to the nucleotide residue or nucleoside monomer to produce a nucleic acid. Some embodiments herein describe a single monomer addition step of the synthesis protocol, where the above process may be reiterated with additional monomers as desired to produce a polymer of desired length and sequence. Optional capping steps may be performed, for example, either prior to and/or after an oxidation step, where unreacted hydroxyls of the first nucleotide residue or nucleoside monomer may be capped, for example with acetic anhydride solution. These additional monomers may be 2'-thionocarbamate protected monomers or protected 2'-deoxy-monomers or non-natural protected monomers, i.e. modified monomers (for example: 2'-fluoro 2'-O-methyl, 2'-methyloxyethyl (2'-MOE), 2'-Locked Nucleic Acid (2'-LNA) etc.; where the modification can be anywhere on the nucleotide structure including the base, as described in the definition of modified nucleotides). Such incorporation of modified nucleotides provides a variety of modified polynucleotides.

RNA Deprotection

RNA may be 2'-deprotected using amines in organic solvent. The base catalyzed mechanism for the degradation of RNA depends on the ability of the base to deprotonate the hydroxyl to a sufficient extent such that the cyclization and cleavage reaction can occur at a significant rate. An example of an amine that may be used is ethylene diamine (EDA).

Exposing RNA to solutions of amine bases in organic solvents may perform deprotection of RNA of both the exocyclic amine protecting groups as well as the 2'-hydroxyl protecting group. The deprotection of the exocyclic amines and the 2'-hydroxyl can be performed simultaneously or sequentially. So long as the solutions do not contain enough water to significantly change the favorable pKa differential of the amines and hydroxyls, with the appropriate choice of protecting groups the degradation of the RNA will be very slow relative to the rate of deprotection. The exposure of RNA to amines bases, including EDA, may also perform the deprotection of the 2-cyanoethyl group on the phosphorous moiety and the cleavage of the succinimidyl linker that attaches the RNA to the solid support, therefore releasing the RNA from the solid support.

In another embodiment there is a significant advantage to delivering solutions of amine bases in appropriate organic solvents or in the gas phase is that although the linker that covalently attaches the RNA to the surface of the solid support may be cleaved by bases such as ammonia, the RNA itself will not migrate off of the resin. In many organic solvents, for example isopropanol and acetonitrile, RNA is not appreciably soluble and/or will remain adsorbed or associated with the solid support. This is in contrast to treatment of a solid support with solutions of amines in water or DMSO, which cause cleavage of the linker and subsequent dissolution of the RNA into the water or DMSO solution.

In an embodiment thionocarbonates and thionocarbamates can be cleaved from the 2'-hydroxyl of synthetic RNA with amines not resulting in the destruction of the desired RNA.

Reaction with 1,2-Diamino Compounds.

Compounds containing a 1,2-diamino functionality, e.g., such as ethylene diamine (EDA), react with 2'-O-(1,1-dioxo-1$\lambda^6$-thiomorpholine-4-carbothioate) protected RNA to give the desired fully deprotected product (below):

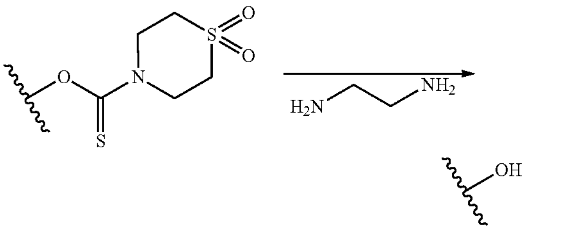

RNA with 2'-deprotected hydroxyl

As an example, a 100mer RNA oligomer was synthesized using a riboG monomer (rG(hyn)) protected on the $N^2$ exocyclic amino group with a hydrocinnamoyl moiety in accordance with Formula VI, wherein $R^4$ is phenyl, Q is guanine, and $R^3$ is thiomorpholine-4-carbothioate (TC group), protecting group. A time-course on the deprotection of the RNA oligomer was run with 1,2-ethylene diamine (EDA) treatment at room temperature to determine deprotection characteristics. Time points were taken every 15 minutes up to 5 hours.

No detectable hydrocinnamoyl guanine protected oligo was observed by mass spectrometry. Thus, indicating that hydrocinnamoyl is suitably labile. Further, no unusual impurities were observed indicating that hydrocinnamoyl stably protects during oligo synthesis. Deprotection of the TC group was complete at 1.75 hours and rU depyrimidination was reduced by greater than 50% relative to isobutyryl deprotection requirements. Results of the time course for 100mer rG(hcin)-RNA is shown in FIG. 1. The experiment was repeated at 40° C., showing that deprotection could similarly be cut in half at elevated temperatures. Results of the time course at the elevated temperature is shown in FIG. 2 and compared to a control 100mer RNA prepared with rG(ibu).

The chemical synthesis of mixed sequence RNAs, 20 nucleotides and 100 nucleotides in length, was accomplished using the methods described in Dellinger, et. al. J. Am. Chem. Soc. 2011, 133, 30, 11540-11556 on solid support, controlled pore glass. Each RNA 100mer contained either the four standard 2'-TC RNA monomers: $N^2$-isobutyryl rG(ibu), $N^6$-benzoyl adenosine (rA(bz)), uridine residues (rU) and $N^4$-acetyl cytidine (rC(ac)), or the three standard 2'-TC RNA monomers rA(bz), rC(ac), rU and a non-standard 2'-TC rG phosphoramidite as disclosed herein (Formula VI) namely $N^2$-hydrocinnamoyl rG (abbreviated as rG(hyn)), or $N^2$-[3-(cyclopentyl)propanoyl] rG (rG(cpp)). The various synthesized RNAs were then deprotected and cleaved in different conditions at 20° C. (room temperature) or at higher temperatures (30° C. to 50° C.) using neat ethylene diamine or a mixture of ethylene diamine (80% to 90%) in an organic solvent (such as toluene), by adding the ethylene diamine or mixture directly to the resulting solid support and let for different periods of time (30 mins to 6 hours), The reaction was stopped by washing the ethylene diamine from the controlled pore glass with anhydrous acetonitrile, and then eluting the crude RNA products using a 0.1M sodium acetate solution, pH 7.0 with 10% acetonitrile. The RNA products were analyzed using an Agilent 6545 quadrupole time-of-flight liquid chromatogram, mass spectrometer. A time course and a comparison study was performed to evaluate the completion of deprotection of the different RNA products under various conditions and to compare their impurities profile. The rates of removal of each protecting group from the $N^2$-exocyclic amino guanosine residue was estimated by examining the extracted mass spectrum of the partially deprotected oligonucleotides and were reported as estimated half-life times ($T_{1/2}$) (FIGS. 3-4). The comparison of the deprotection of the various RNA products synthesized with different $N^2$-protected rG 2'-TC monomers, shows that both rG(hyn) and rG(cpp) shorten significantly the time of complete deprotection of the 100-mer RNA from 2.5 hours when using standard rG(ibu) monomers to a 75 mins time, when using the non-standard 2'-TC rG monomers rG(cpp). Moreover, the shorter deprotection time obtained for the 100-mer RNA oligonucleotide synthesized with the new rG(cpp) monomers, allows to decrease significantly the amounts of shortmer fragment impurities yielding to a significant higher percentage of full length product as shown in FIG. 5. Additionally, the impurities profiles exhibited on the chromatograms of RNA products made with the non-standard monomers rG(cpp) show up to 50% reduction in the depyrimidinations byproducts as compared to the impurities profiles obtained with the standard rG(ibu) RNA products (FIG. 6).

Nucleic Acid Products.

Further disclosed are nucleic acid products of the methods disclosed above. The nucleic acid products, e.g., RNA or oligonucleotides comprising ribonucleotides, may vary in size, ranging in certain embodiments from 2 to 200 or more monomeric units in length, such as 2 to 100 or more monomeric units in length, including 2 to 50 or more monomeric units in length. In certain embodiments, the size of the product nucleic acids ranges from 2 to 25 monomeric units in length, e.g., 15 to 25 monomeric units in length, such as 17 to 23 monomeric units in length, including 19, 20, 21, or 22 monomeric units in length.

In certain embodiments, nucleic acid products of the invention have the structure of Formula (VIII):

Formula VIII

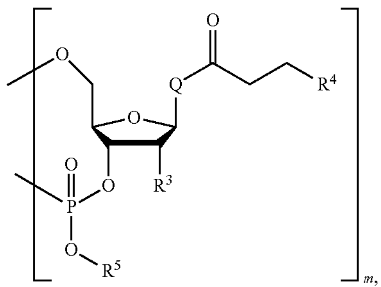

wherein $R^3$ is H, F, O—$C_{1-6}$ alkyl, O-MOE, or a O-thiocarbon protecting group;

wherein Q is a heterocyclic base;

wherein $R^4$ is a cyclic hydrocarbon;

wherein $R^5$ is selected from the group consisting of hydrogen, a hydrocarbyl, a substituted hydrocarbyl, an aryl, and a substituted aryl; and wherein m is an integer of at least 1.

Each of $R^3$, Q, and $R^4$ can be independently any of the variations described above with regard to the compound having the structure of Formula I. $R^5$ is typically a 2-cyanoethyl or a methyl group.

Although described in connection with preferred embodiments thereof, it will be appreciated by those skilled in the art that additions, deletions, modifications, and substitutions not specifically described may be made without departure from the scope of the invention as defined in the appended claims.

EXAMPLES

Synthesis of $N^2$-(3-CYCLOALKYL)PROPANOYL-GUANOSINE Derivatives (1A, 1B, 1C)

To synthesize the following derivatives, N[$^2$-(3-cyclopentyl)propanoyl]-guanosine (1A), N[$^2$-(3-cyclohexyl)propanoyl]-guanosine (1B), N[$^2$-hydrocinnamoyl-guanosine (1C), the following acyl chloride reagents 3-(cyclopentyl) propanoyl chloride (A), 3-(cyclohexyl)propanoyl chloride (B) and hydrocinnamoyl chloride (C) were respectively used in the reactions detailed below.

Guanosine hydrate (1.5 g, 5 mmol) was placed in a 500 mL round bottom flask and dried three times by azeotropic evaporation with 25 mL portions of anhydrous pyridine. The residual was resuspended in 25 mL anhydrous pyridine and anhydrous dichloromethane (100 mL) under an argon atmosphere. The mixture was cooled in an ice bath/water bath and stirred using a magnetic stir bar. Trimethylsilyl chloride (TMSCl, 5.7 mL, 45 mmol, 9 eq) was added dropwise over 2 min. The flask was removed from the ice bath and allowed to warm to room temperature then stirred for 2 hr. After 2 hours, the nucleoside was completely dissolved resulting in a clear colorless liquid. The flask was cooled again in an ice/water bath, and the corresponding acyl chloride[(A,B,C)] (5.5 mmol, 1.1 eq) was added dropwise over 10 min. The mixture was stirred at 0° C. for 3 hours. The excess acid chloride was neutralized by the addition of methanol (20 mL) and the solution was stirred at room temperature for 12 hr. After 12 hours, the methanol and dichloromethane were removed under vacuum on a rotary evaporator, leaving the residual as a viscous oil in pyridine. 200 ml of water was added to the solution, the flask was fitted with a Fredrick's reflux condenser and a heating mantel. The reaction mixture was heated to reflux and allowed to reflux for 1 hr. The heating mantel was removed, and the solution allowed to cool to room temperature resulting in a white precipitate. The precipitate was filtered and dried under vacuum giving a flocculant white powder. In each case the powder was analyzed by $^{1}H$ NMR, $^{13}C$ NMR and Mass Spectroscopy giving near quantitative yield of the desired $N^2$-(3-cycloalkyl)propanoyl protected guanosine derivatives (1A, 1B, 1C).

Synthesis of 3',5'-TETRAISOPROPYLDISILOXANE-$N^2$-(3-CYCLOALKYL)PROPANOYL-GUANOSINE Derivatives (2A, 2B, 2C)

The general experimental protocol described below was used to synthesize the following products $N^2$-(3-cyclopentyl)propanoyl-3',5'-tetraisopropyldisiloxane guanosine (2A), $N^2$-(3-cyclohexyl)propanoyl-3',5'-tetraisopropyldisiloxane-guanosine (2B), $N^2$-hydrocinnamoyl-3',5'-tetraisopropyldisiloxane guanosine (2C) using respectively compounds 1A, 1B, 1C as starting material.

$N^2$-protected-guanosine 16.1 g (39.5 mmol) (1 eq) was dried by azeotropic evaporation, three times, using a rotary evaporator with 200 ml of anhydrous pyridine. The resulting white powder was then dissolved in 400 ml of anhydrous pyridine and cooled to 0° C. using an ice/water bath. To this cooled solution 1,3-dichloro-1,1,3,3-tetraisopropyl-disiloxane 12.6 ml (39.5 mmol) (1 eq) was added dropwise with stirring. After the addition was complete, the ice bath was removed, and the reaction allowed to warm to room temperature. The extent of the reaction was monitored by TLC (5% methanol in methylene chloride). In all cases, after 2 hours the TLC showed that all starting material was consumed. The reaction mixture was evaporated to an oil on a rotary evaporator. The residual pyridine was removed by azeotropic evaporation with, three times, with 200 ml of anhydrous toluene. The residual was dissolved in dichloromethane (400 ml) and transferred to a separatory funnel. The dichloromethane solution extracted with 300 ml of a saturated solution of sodium bicarbonate followed by 300 ml of water, and then the dichloromethane was extracted with brine. The methylene chloride layer was separated and dried over anhydrous sodium sulfate. The methylene chloride was removed by evaporation on a rotary evaporator and the residual was dissolved with heating to reflux in anhydrous acetonitrile. The product was allowed to cool room temperature, then placed in a freezer at −20° C. overnight, resulting in the formation of a while crystalline solid which was isolated by filtration and dried under vacuum, giving a yield of 66% to 88%. In each case the crystalized product was analyzed by $^{1}H$ NMR, $^{13}C$ NMR, and Mass Spectroscopy resulting in high purity, $N^2$-protected-3',5'-tetraisopropyl-disiloxane guanosine (2A, 2B, 2C) products.

Synthesis of 3',5'-O-(TETRAISOPROPYLDISILOXANE-1,3-DIYL)-2'-O-(1,1-DIOXO1Λ6-THIOMORPHOLINE-4-CARBOTHIOATE) $N^2$-[3-(CYCLOALKYL)PROPANOYL]-GUANOSINE Compounds (3A, 3B, 3C)

The general experimental protocol described below was used to synthesize the following products $N^2$-[3-(cyclopentyl)propanoyl]-2'-O-TC guanosine (3A), $N^2$-[3-(cyclohexyl) propanoyl]-2'-O-TC guanosine (3B), $N^2$-hydrocinnamoyl-2'-O-TC guanosine (3C) using respectively compounds 2A, 2B, 2C as starting material. $N^2$-protected-3',5'-tetraisopropyldisiloxane-guanosine (100 mmol) was dissolved in DCM (200 ml, 0.5M) and 1,1-thiocarbonyldiimidazole (1.05 eq., 18.7 g, 105 mmol) was added and stirred for 2 h at ambient temperature. Acetonitrile (100 ml) and thiomorpholine-1,1-dioxide (14.87 g, 110 mmol) was added to the reaction mixture and heated to approximately 50° C. until the solution became clear then stirred for at ambient temperature for 4 hours. The resulting product crystalized from the reaction mixture. The crystals were collected by filtration and then recrystallized from acetonitrile. In each case the crystalized product was analyzed by $^{1}H$ NMR, $^{13}C$ NMR, and Mass Spectroscopy resulting in high purity 3',5'-O-(Tetraisopropyldisiloxane-1,3-diyl)-2'-O-(1,1-dioxo1λ6-thiomorpholine-4-carbothioate)-$N^2$-protected-guanosine derivatives (3A, 3B, 3C).

Removal of the 3',5'-O-(TETRAISOPROPYLDISILOXANE-1,3-DIYL) Protecting Group (Compounds 4A, 4B, 4C)

3',5'-O-(Tetraisopropyldisiloxane-1,3-diyl)-2'-O-(1,1-dioxo1λ6-thiomorpholine-4-carbothioate)-$N^2$-(3-cycloalkyl)propanoyl-guanosine compounds obtained above (3A, 3B, 3C) were each treated with HF/pyridine to remove the TIPS protecting group and yield respectively 2'-O-(1,1-dioxo1λ6-thiomorpholine-4-carbothioate)-$N^2$-[3-(cyclopentyl)propanoyl] guanosine (4A), 2'-O-(1,1-dioxo1λ6-thiomorpholine-4-carbothioate)-$N^2$-[3-(cyclohexyl)propanoyl] guanosine (4B) and), 2'-O-(1,1-dioxo1λ6-thiomorpholine-4-carbothioate)-$N^2$-hydrocinnamoyl guanosine (4C), according to the following general procedure. 3',5'-O-(Tetraisopropyldisiloxane-1,3-diyl)-2'-O-(1,1-dioxo1λ6-thiomorpholine-4-carbothioate)-$N^2$-protected-guanosine (100 mmol) was suspended in 2-methyltetrahydrofuran (2-MTHF) (300 ml, 0.33M) and pyridine (48.65 ml, 604 mmol). The reaction was cooled to 0° C. and hydrogen fluoride pyridine (HFxPy) (31.37 ml, 1208 mmol) was added with stirring. After addition of the HF solution the ice bath was removed, and the reaction allowed to warm to room temperature. The reaction solution was stirred for 2 h at ambient temperature then more 2-MTHF (200 ml) was added and the solution extracted with water (350 ml). The aqueous layer was back extracted with 2-MTHF (2×250 ml). The organic layers were combined, dried with $Na_2SO_4$, filtered, evaporated and dried over night at room temperature on a vacuum pump resulting in a yield of ≈70% in all cases.

Synthesis of 5'-O-(4,4'-DIMETHOXYTRITYL)-2'-O-(1,1-DIOXO1$\lambda^6$-THIOMORPHOLINE-4-CARBOTHIOATE)-$N^2$-[3-(CYCLOALKYL)PROPANOYL]-GUANOSINE Derivatives (5A, 5B, 5C)

Compounds 5A, 5B, 5C were synthesized following the general procedure described below starting with their respective precursors 4A, 4B, and 4C. 2'-O-(1,1-dioxo1λ6-thiomorpholine-4-carbothioate)-$N^2$-protected-guanosine (4A, 4B, 4C, 70 mmol) was suspended in 2-MTHF/DCM (1400 ml, 0.05M) and stirred for 30 min, then N-methyl morpholine (NMM) (8.47 ml, 77 mmol) and 4,4'-dimethoxytrityl chloride (26.09 g, 77 mmol) were added in small portions while stirring. The reaction was complete in 40 min. The products (5A, 5B, 5C), without isolation, were then directly phosphitylated to produce the 2'-O-(1,1-dioxo1$\lambda^6$-thiomorpholine-4-carbothioate)-5'-O-(4,4'-dimethoxytrityl)-$N^2$-protected-guanosine-3'-O—(O-cyanoethyl)-N,N-diisopropyl-phosphoramidite as described herein after.

Synthesis of 5'-O-(4,4'-DIMETHOXYTRITYL)-2'-O-(1,1-DIOXO1$\lambda^6$-THIOMORPHOLINE-4-CARBOTHIOATE)-$N^2$-[3-(CYCLOALKYL)PROPANOYL]-GUANOSINE 3'-O-(2-CYANOETHYL)-N,N-DIISOPROPYL-PHOSPHORAMIDITE Derivatives (6A, 6B, 6C)

N-Methylmorpholine (10 ml, 91 mmol) was added to the previous reaction mixture containing compound 5A or 5B, or 5C, followed by addition of 2-cyanoethyl N,N-diisopropylchlorophosphoramidite (18.74 ml, 84 mmol) then stirred at RT for 3.5 h. DCM (150 ml) was added and the mixture was extracted with saturated $NaHCO_3$ (500 ml). The organic phase was dried over anhydrous sodium sulfate, then evaporated on a rotary evaporator resulting in a viscous oil. The oil was dissolved in a minimum volume of dichloromethane and added dropwise with stirring to a 2-liter Kjeldahl flask containing hexanes (400 ml) resulting in a flocculent suspension. The suspension was placed in a −20° C. freezer overnight to settle to a cake on the bottom of the flask. Solvent was decanted and the crude product was immediately dissolved in dry DCM and loaded to a silica gel column pre-neutralized with triethylamine (300 g silica gel). Then crude product was introduced carefully on top of the column and eluted with acetone; 20% (1 L), 25% (2 L), 30% (2 L), 40% (4 L) and 45% (2 L) acetone/hexanes. The product fractions were analyzed using TLC or HPLC. Fractions containing the desired product were collated and evaporated to dryness on a rotary evaporator producing a white foam with an overall yield of 65% to 75%. The product was analyzed by $^1H$ NMR, $^{13}C$ NMR, and Mass Spectroscopy and the purity was determined using $^{31}P$ NMR, and HPLC. All products, 5'-O-(4,4'-dimethoxytrityl)-2'-O-(1,1-dioxo1$\lambda^6$-thiomorpholine-4-carbothioate)-$N^2$-[3-(cyclopentyl)propanoyl]-guanosine 3'-O-(2-cyanoethyl)-N,N-diisopropyl-phosphoramidite (6A, rG(cpp)), 5'-O-(4,4'-dimethoxytrityl)-2'-O-(1,1-dioxo1$\lambda^6$-thiomorpholine-4-carbothioate)-$N^2$-[3-(cyclohexyl)propanoyl]-guanosine 3'-O-(2-cyanoethyl)-N,N-diisopropyl-phosphoramidite (6B), 5'-O-(4,4'-dimethoxytrityl)-2'-O-(1,1-dioxo1$\lambda^6$-thiomorpholine-4-carbothioate)-$N^2$-hydrocinnamoyl-guanosine 3'-O-(2-cyanoethyl)-N,N-diisopropyl-phosphoramidite (6C, rG(hyn)) gave ≥95% purity by both methods.

Oligonucleotides Synthesis and Deprotection 20-mers RNA oligonucleotides and 100-mers RNA oligonucleotides were synthesized using the TC Chemistry, on a 2000A CPG support from Prime Synthesis (LGC), using Dr. Oligo 48 synthesizer from Biolytic Lab Performance Inc. The standard 2'-TC RNA phosphoramidites (rA(bz), rG(ib), rC(ac) and rU) were purchased from Sigma-Aldrich. The rG(cpp) 2'-O-TC-3'-O-[(2-cyanoethyl)-N,N-diisopropyl] phosphoramidite (compound 6A) and rG(hcin) 2'-O-TC-3'-O-[(2-cyanoethyl)-N,N-diisopropyl]phosphoramidite (6C) were synthesized as described herein. All other standard RNA synthesis reagents were purchased from Glen Research and Honeywell. The chemical synthesis of mixed sequence RNAs, 20 and 100 nucleotides in length, was accomplished using the methods described in Dellinger, et. al. J. Am. Chem. Soc. 2011, 133, 30, 11540-11556. Each RNA (20 and 100mers) contained the four RNA monomers guanosine residues, adenosine residues, uridine residues and cytidine residues, and were deprotected in different conditions at 20° C. (room temperature) or at higher temperatures (30° C. to 50° C.) using neet ethylene diamine, by adding the ethylene diamine directly to the resulting solid support. A time course (30 min to >6 hours) was performed to evaluate the completion of the $N^2$-exocyclic amines deprotection. The reaction was stopped by washing the ethylene diamine from the controlled pore glass with anhydrous acetonitrile, and then eluting the crude RNA products using a 0.1M sodium acetate solution, pH 7.0 with 10% acetonitrile. The RNA products were analyzed using an Agilent 6545 quadrupole time-of-flight liquid chromatogram, mass spectrometer. The time course and various conditions used for the deprotection of the RNA products was performed to compare the ease, the completion of the deprotection of the RNA products prepared with rG(ibu), rG(cpp) and rG(hyn) and to compare their impurities profile.

What is claimed is:

1. A compound having the structure of Formula I:

Formula I

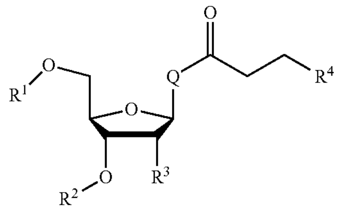

wherein each of $R^1$ or $R^2$ is independently selected from the group consisting of a protecting group and a phosphoramidite group, provided $R^1$ and $R^2$ are not both protecting groups;

wherein $R^3$ is H, F, O—$C_{1-6}$ alkyl, O-MOE, or O-thiocarbon protecting group;

wherein Q is a heterocyclic base; and wherein $R^4$ is cyclopentyl or cyclohexyl.

2. The compound according to claim 1, wherein said compound has the structure of Formula Ia:

Formula Ia

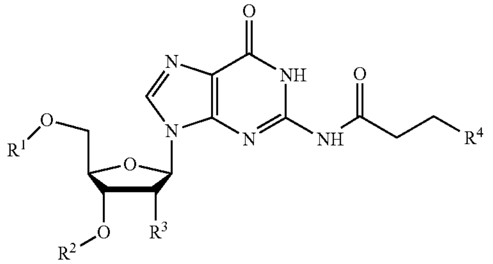

wherein each of $R^1$ or $R^2$ is independently selected from the group consisting of a protecting group and a phosphoramidite group, provided $R^1$ and $R^2$ are not both protecting groups;

wherein $R^3$ is H, F, O—$C_{1-6}$ alkyl, O-MOE, or O-thiocarbon protecting group; and wherein $R^4$ is cyclopentyl or cyclohexyl.

3. The compound according to claim 2, wherein $R^1$ and $R^2$ are each independently selected from 4,4'-dimethoxytrityl (DMT) and 2-cyanoethyl-(N,N-diisopropylamino)-phosphoramidite.

4. The compound according to claim 3, wherein $R^4$ is cyclopentyl and wherein $R^3$ is O-TC:

O-TC

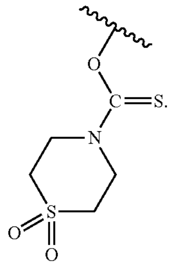

5. The compound according to claim 1, wherein said compound has the structure of Formula Ib:

Formula Ib

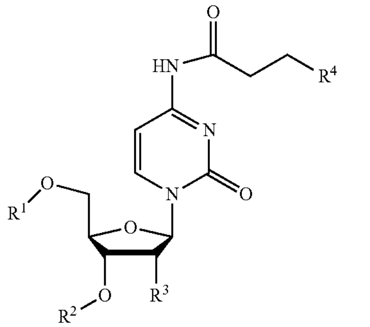

wherein each of $R^1$ or $R^2$ is independently selected from the group consisting of a protecting group and a phosphoramidite group, provided $R^1$ and $R^2$ are not both protecting groups;

wherein $R^3$ is H, F, O—$C_{1-6}$ alkyl, O-MOE, or O-thiocarbon protecting group; and wherein $R^4$ is cyclopentyl or cyclohexyl.

6. The compound according to claim 5, wherein $R^1$ and $R^2$ are each independently selected from 4,4'-dimethoxytrityl (DMT) and 2-cyanoethyl-(N,N-diisopropylamino)-phosphoramidite.

7. The compound according to claim 6, wherein $R^4$ is cyclopentyl and wherein $R^3$ is O-TC:

O-TC

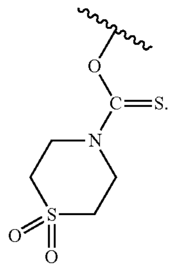

8. A method comprising:

contacting a nucleoside residue comprising a 5' or 3' unprotected hydroxyl with a protected nucleotide monomer having the structure of Formula I:

Formula I

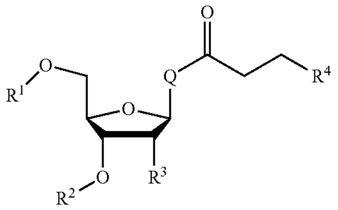

wherein each of $R^1$ or $R^2$ is independently selected from the group consisting of a protecting group and a phosphoramidite group, provided $R^1$ and $R^2$ are not both protecting groups;

wherein $R^3$ is H, F, O—$C_{1-6}$ alkyl, O-MOE or O-thiocarbon protecting group;

wherein Q is a heterocyclic base; and wherein $R^4$ is cyclopentyl or cyclohexyl, under conditions sufficient to covalently bond said phosphoramidite group of said protected nucleotide monomer to said unprotected hydroxyl group of said nucleoside residue and produce an internucleotide bond.

9. The method according to claim 8, wherein said method further comprises exposing said internucleotide bond to an oxidizing agent.

10. The method according to claim 8, wherein said method further comprises removing said thiocarbon protecting group.

11. The method according to claim 8, wherein said nucleoside residue is covalently bound to a solid support.

12. The method according to claim 11, wherein said method further comprises cleaving said nucleic acid from said solid support to produce a free nucleic acid.

13. The method according to claim 8, wherein the thiocarbon protecting group is selected from the group of structures consisting of:

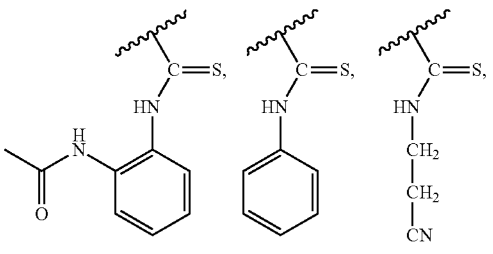

-continued

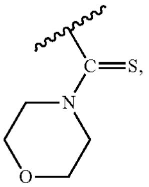

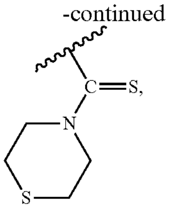

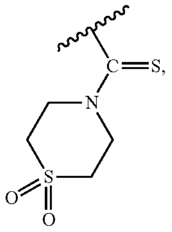

and

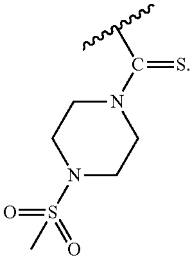

14. The method according to claim 13, wherein the thiocarbon protecting group is

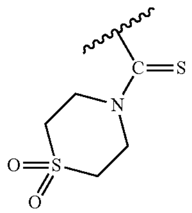 [SMILES: *C(=S)N1CCS(=O)(=O)CC1]

and wherein each of $R^1$ or $R^2$ is independently selected from the group consisting of 4,4'-dimethoxytrityl (DMT) and 2-cyanoethyl-(N,N-diisopropylamine)-phosphoramidite.

15. The method according to claim 14, wherein Q is G or C.

16. The method according to claim 15, wherein Q is G.

17. A protected nucleic acid comprising the structure of Formula VIII:

Formula VIII

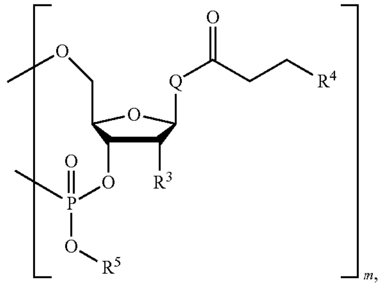

wherein $R^3$ is H, F, O—$C_{1-6}$ alkyl, O-MOE, or O-thiocarbon protecting group;

wherein Q is a heterocyclic base;

wherein $R^4$ is cyclopentyl or cyclohexyl;

wherein $R^5$ is selected from the group consisting of hydrogen, a hydrocarbyl, a substituted hydrocarbyl, an aryl, and a substituted aryl; and wherein m is an integer of at least 1.

18. The protected nucleic acid of claim 17, wherein Q is G, wherein said thiocarbon protecting group is:

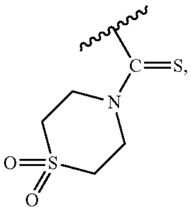 [SMILES: *C(=S)N1CCS(=O)(=O)CC1]

said $R^4$ is cyclopentyl, and said $R^5$ is 2-cyanoethyl or methyl.

* * * * *